(12) United States Patent
Kass

(10) Patent No.: US 11,147,574 B2
(45) Date of Patent: Oct. 19, 2021

(54) SUSPENSION UVULOPALATOPEXY RELATED METHODS, DEVICES, AND APPARATUSES

(71) Applicant: Erik S. Kass, Bethesda, MD (US)

(72) Inventor: Erik S. Kass, Bethesda, MD (US)

( * ) Notice: Subject to any disclaimer, the term of this patent is extended or adjusted under 35 U.S.C. 154(b) by 565 days.

(21) Appl. No.: 15/723,317

(22) Filed: Oct. 3, 2017

(65) Prior Publication Data
US 2018/0092654 A1    Apr. 5, 2018

Related U.S. Application Data

(60) Provisional application No. 62/403,848, filed on Oct. 4, 2016.

(51) Int. Cl.
*A61B 17/24*    (2006.01)
*A61F 5/56*     (2006.01)
(Continued)

(52) U.S. Cl.
CPC .......... *A61B 17/24* (2013.01); *A61B 17/0401* (2013.01); *A61B 17/07207* (2013.01); *A61F 5/56* (2013.01); *A61B 17/0466* (2013.01); *A61B 17/32053* (2013.01); *A61B 2017/00477* (2013.01); *A61B 2017/00566* (2013.01); *A61B 2017/00862* (2013.01); *A61B 2017/00867* (2013.01); *A61B 2017/00876* (2013.01);
(Continued)

(58) Field of Classification Search
CPC . A61F 5/56; A61F 5/566; A61B 17/24; A61B 2017/248; A61B 17/0401; A61B 5/4818; A61B 2017/00004; A61B 2017/0408; A61B 2017/0464; A61B 2017/06052

USPC ........... 128/846, 848, 897, 200.24; 606/144, 606/222, 228, 230
See application file for complete search history.

(56) References Cited

U.S. PATENT DOCUMENTS 7,073,505 B2    7/2006    Nelson et al.
8,622,061 B2    1/2014    Zhang et al.
(Continued)

OTHER PUBLICATIONS

Shannon Larratt, Apr. 13, 2006, Uvula_Piercing_2 (image) (Year: 2006).*

(Continued)

*Primary Examiner* — Rachael E Bredefeld
*Assistant Examiner* — Trisha Talapatra
(74) *Attorney, Agent, or Firm* — Muir Patent Law, PLLC

(57) ABSTRACT

The disclosed embodiments includes apparatuses, devices, and methods for treating a breathing disorder, comprising: inserting a first target oral stud into a first location of an anchor structure, the first target oral stud including a target stud shaft, a target anterior anchor, and a target posterior anchor, wherein the target stud shaft (or suture) is positioned within the tissue of the anchor structure. The embodiments further comprise inserting a first support oral stud into a first location of a support structure, the first support oral stud including a support stud shaft (or suture), a support anterior anchor, and a support posterior anchor, wherein the support stud shaft is positioned within tissue of the support structure. Further, the embodiments comprise connecting, using at least one first connector, the target anterior anchor with the support anterior anchor.

21 Claims, 30 Drawing Sheets

(51) Int. Cl.
*A61B 17/072* (2006.01)
*A61B 17/04* (2006.01)
*A61B 17/3205* (2006.01)
*A61B 17/00* (2006.01)
*A61B 17/06* (2006.01)

(52) U.S. Cl.
CPC ............. *A61B 2017/0408* (2013.01); *A61B 2017/0409* (2013.01); *A61B 2017/0414* (2013.01); *A61B 2017/0419* (2013.01); *A61B 2017/0445* (2013.01); *A61B 2017/0448* (2013.01); *A61B 2017/0464* (2013.01); *A61B 2017/0618* (2013.01); *A61B 2017/07285* (2013.01); *A61B 2017/248* (2013.01); *A61B 2217/005* (2013.01)

(56) References Cited

U.S. PATENT DOCUMENTS

| | | | |
|---|---|---|---|
| 2004/0045555 A1* | 3/2004 | Nelson | A61F 5/566 128/848 |
| 2005/0279365 A1 | 12/2005 | Armijo et al. | |
| 2007/0000497 A1* | 1/2007 | Boucher | A61F 5/566 128/848 |
| 2008/0066769 A1* | 3/2008 | Dineen | A61F 5/566 128/897 |
| 2008/0097380 A1* | 4/2008 | Li | A61F 5/566 604/506 |
| 2008/0188947 A1* | 8/2008 | Sanders | A61B 17/0401 623/23.72 |
| 2009/0014012 A1* | 1/2009 | Sanders | A61N 1/0548 128/848 |
| 2011/0144421 A1* | 6/2011 | Gillis | A61F 5/56 600/37 |
| 2012/0227748 A1 | 9/2012 | Sanders | |
| 2014/0014116 A1* | 1/2014 | Gillis | A61F 5/566 128/848 |
| 2015/0088166 A1 | 3/2015 | Krespi et al. | |
| 2016/0022470 A1* | 1/2016 | Gillis | A61F 5/56 128/848 |
| 2016/0220411 A1 | 8/2016 | Krespi et al. | |

OTHER PUBLICATIONS

Sheila S. Price, Maurice W. Lewis, Body Piercing Involving Oral Sites, Jul. 1997, The Journal of the America Dental Association, vol. 128, Issue 7, pp. 1017-1020 (Year: 1997).*

Enoz M, Japena JF, Inancli HM, Hafiz G, Modified sling snoreplasty: double triangle shaped suture uvulopalatopexy, 2010, Journal Kulak Burun Bogaz Ihtis Derg, pp. 51-55 (Year: 2010).*

* cited by examiner

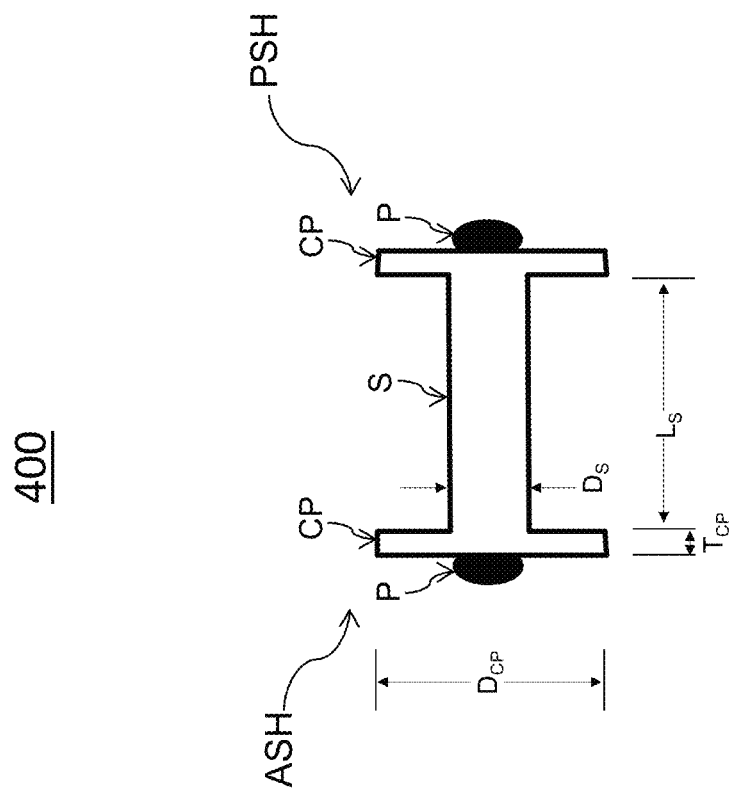

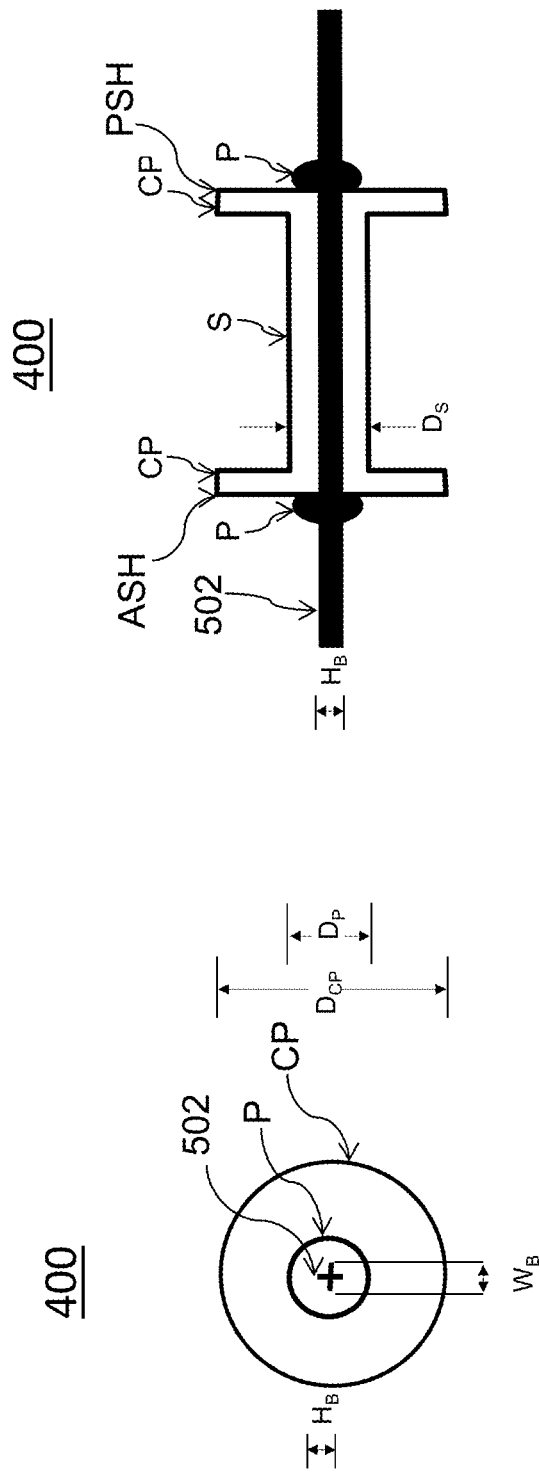

SUSPENSION UVULOPALATOPEXY RELATED METHODS, DEVICES, AND APPARATUSES

CROSS-REFERENCE TO RELATED APPLICATION

This application claims the benefit of priority under 35 U.S.C. § 119 to U.S. Provisional Application No. 62/403,848, filed Oct. 4, 2016, in the United States Patent and Trademark Office, the entire contents of which is hereby incorporated by reference.

FIELD

This present disclosure relates to suspension uvulopalatopexy and cosmetic piercings. Particularly, the present disclosure relates to suspension uvulopalatopexy to combat snoring and/or mitigate obstructive sleep apnea.

BACKGROUND

Generally, obstructive sleep apnea is a breathing disorder characterized by snoring and apnea caused by upper airway collapse and obstruction during sleep. During normal sleep, the muscles of the upper part of the throat keep the airway open to permit air flow into the lungs. With obstructive sleep apnea, the muscles of the soft palate, the base of tongue and the uvula, can relax during sleep. In some cases, the relaxed tissues may vibrate as air flows past the tissues during breathing, resulting in snoring. In more serious cases, the airway can become blocked, making breathing labored and noisy, or even causing it to stop altogether. These breathing pauses are almost always accompanied by snoring between apnea episodes.

Obstructive sleep apnea can result in diminished health, in part, because the lack of air intake into the lungs results in lower levels of oxygen and increased levels of carbon dioxide in the blood. The altered levels of oxygen and carbon dioxide alert the brain to resume breathing and cause arousal. The frequent interruptions of deep, restorative sleep often lead to early morning headaches, excessive daytime sleepiness, depression, irritability, and difficulty with learning and memory. For those with moderate or severe obstructive sleep apnea, there is an increased incidence of diabetes, heart attacks, hypertension and strokes.

The disclosed embodiments provide for simple, cost-effective, minimally invasive devices and methods to reduce or prevent snoring and obstructive sleep apnea with a focus on the soft palate, tonsil, and tongue base.

SUMMARY

In some exemplary embodiments, the present disclosure is directed to a method for treatment using suspension uvulopalatopexy, comprising: inserting a uvular stud into a predetermined location of a uvula, wherein the uvular stud includes a uvular stud shaft, a first uvular stud head, and a second uvular stud head, wherein the first and second uvular stud heads are respectively located at opposite ends of the uvular stud shaft and external to the uvula, and wherein the uvular stud shaft is positioned within the uvula; inserting at least a first palate stud into a first location of a palate, wherein the first palate stud includes a palate stud shaft, a first palate stud head, and a second palate stud head, wherein the first and second palate stud heads are respectively located at opposite ends of the palate stud shaft and external to the palate, and wherein the palate stud shaft is positioned within the palate; and connecting, via a connector, the uvular stud with the palate stud, wherein the connector has a first connecting piece connected to the first uvular stud head and a second connecting piece connect to the first palate stud head.

In further exemplary embodiments, the disclosure is directed to a method for treatment using suspension uvulopalatopexy, comprising: inserting a first target oral stud into a first location of an anchor structure, wherein the first target oral stud includes a first target stud shaft, a first target anterior stud head, and a first target posterior stud head, wherein the first target anterior stud head and the first target posterior stud head are respectively located at opposite ends of the first target stud shaft and external to tissue of the anchor structure, and wherein the first target stud shaft is positioned within the tissue of the anchor structure; inserting a first support oral stud into a first location of a support structure, wherein the first support oral stud includes a first support stud shaft, a first support anterior stud head, and a first support posterior stud head, wherein the first support anterior stud head and the first support posterior stud head are respectively located at opposite ends of the first support stud shaft and external to tissue of the support structure, and wherein the first support stud shaft is positioned within tissue of the support structure; and connecting, using at least one first connector, the first target anterior stud head with the first support anterior stud head.

In further exemplary embodiments, the disclosure is directed to an oral stud gun for use in treatment of a breathing disorder, comprising: a barrel having a hollow cylinder and being surrounded by a housing; a blade drive shaft located along a central axis of the barrel and within the housing; a plurality of stud drive shafts surrounding the blade drive shaft; a blade hub configured to hold a blade and control extension and retraction of the blade; a blade hub holding member configured to hold the blade hub; and a sliding stud displacement member configured to move forward and backward along the central axis of the barrel, and provide pressure against an oral stud loaded in the barrel, wherein the sliding stud displacement member is configured to push the oral stud through the barrel in a direction of a target site, and wherein the housing includes a plurality of suction holes.

In further exemplary embodiments, the disclosure is directed to an oral stud for use in treatment of a breathing disorder, comprising: a stud shaft; an anterior stud head; and a posterior stud head, wherein the anterior head and the posterior head are respectively located at opposite ends of the stud shaft, and wherein the oral stud is formed of at least one or more of a bio-compatible material, an elastic material, or a shape memory material.

BRIEF DESCRIPTION OF THE DRAWINGS

The above and other objects and features will become apparent from the following description with reference to the following figures, wherein like reference numerals refer to like parts throughout the various figures unless otherwise specified. The drawings are not necessarily to scale, emphasis instead being placed upon illustrating the principles of the disclosed embodiments. In the drawings:

FIGS. 4A-4C are schematics of an oral stud for use in suspension uvulopalatopexy, according to certain exemplary embodiments;

FIGS. 5A-5B are schematics of an oral stud with an insertion blade, according to certain exemplary embodiments;

DETAILED DESCRIPTION

Figure 1A:
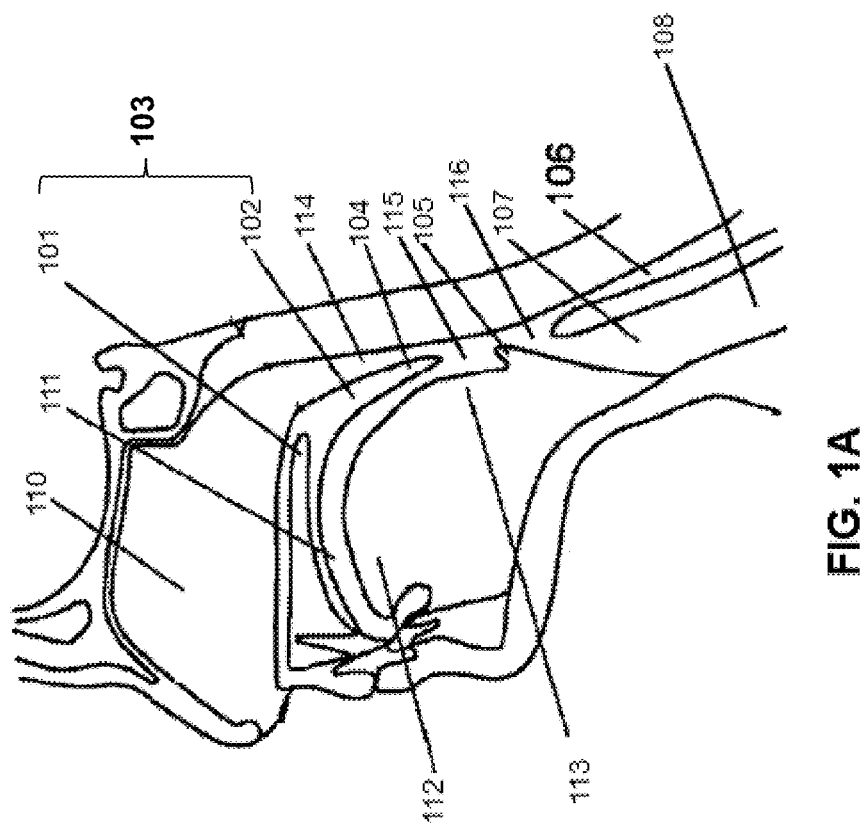
FIG. 1A is a cross-sectional side (saggital) view of a human head during nasal breathing.

Various exemplary embodiments will be described in detail with reference to the accompanying drawings. The inventive concept, however, may be embodied in various different forms, and should not be construed as being limited only to the illustrated embodiments. Accordingly, known processes, elements, and techniques are not described with respect to some of the embodiments of the disclosure. Unless otherwise noted, like reference numerals denote like elements throughout the attached drawings and written description, and thus descriptions will not be repeated. In the drawings, the sizes and relative sizes of layers and regions may be exaggerated for clarity.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising" or "includes" and/or "including," when used in this specification, specify the presence of stated features, regions, integers, steps, operations, elements, components, and/or groups, but do not preclude the presence or addition of one or more other features, regions, integers, steps, operations, elements, components, and/or groups thereof. In addition, unless the context indicates otherwise, steps described in a particular order need not occur in that order. As used herein, the term "and/or" includes any and all combinations of one or more of the associated listed items.

It will be understood that, although the terms "first," "second," "third," etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the disclosure.

As will be understood, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood, all language such as "up to," "at least," "greater than," "less than," and the like include the number recited and refer to ranges which can be subsequently broken down into subranges as discussed above. Finally, as will be understood, a range includes each individual member. Thus, for example, a group having 1-3 members refers to groups having 1, 2, or 3 members.

Similarly, a group having 1-5 members refers to groups having 1, 2, 3, 4, or 5 members, and so forth.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

Figure 1B:
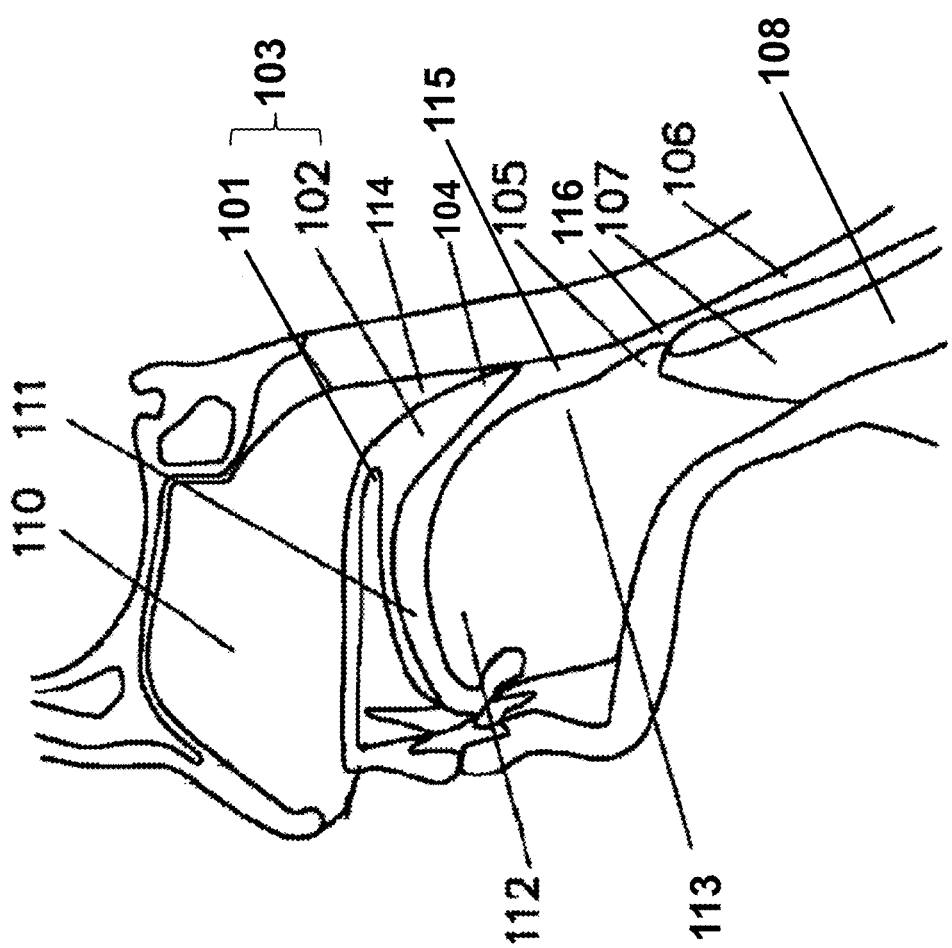
FIG. 1B is a cross-sectional side view of a human head depicting obstruction of the airway.
Figure 1C:
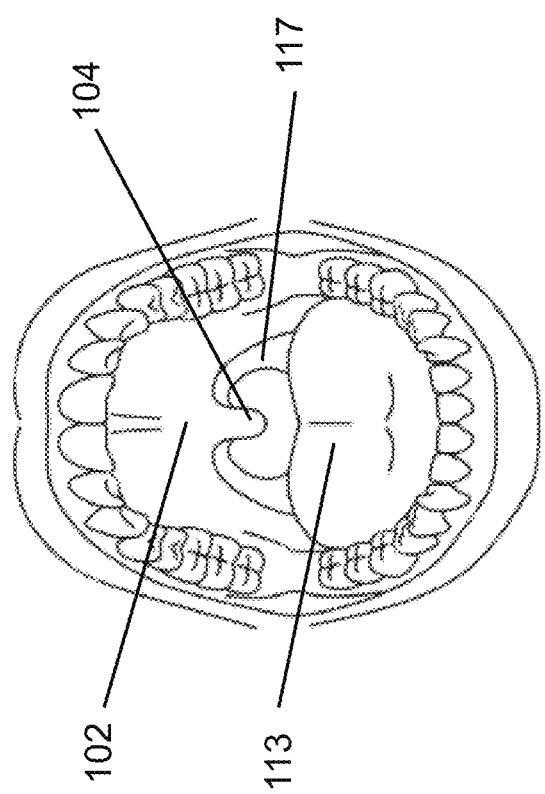
FIG. 1C is a front view of certain features of the upper respiratory system.

FIGS. 1A and 1B are cross-sectional side views of a human head, illustrating the upper respiratory system. FIG. 1C is a front view of certain features of the upper respiratory system. In particular, FIGS. 1A-1C illustrate the structures that perform the functions of breathing and swallowing, including the hard palate 101 and the soft palate 102 (collectively referred to as the palate 103), the uvula 104 (which is contiguous with the lower portion of the soft palate 102), the epiglottis 105, the esophagus 106, the larynx 107, the trachea 108, the nasal cavity 110, the oral cavity (mouth) 111, the tongue 112, the tongue root (base) 113, the pharynx, which is comprised of the nasopharynx 114, the oropharynx 115, and the hypopharynx 116, and the lateral pharyngeal walls 117.

As shown in FIGS. 1A and 1B, the palate 103 is located in the upper portion of the oral cavity 111, and it separates the oral cavity 111 from the nasal cavity 110. The anterior two-thirds of the palate 103 is the bony hard palate 101, and the posterior one-third of the palate 103 is known as the soft palate 102. The soft palate 102, which is comprised of muscle and aponeurosis, is suspended from the posterior border of the hard palate 101 and extends posteroinferiorly. The uvula 104 hangs from the posterior region of the soft palate 102.

The nasopharynx 114, which is located posterosuperior to the soft palate 102, lies posterior to the nasal cavity 110, extending from the base of the skull to the soft palate 102. The oropharynx 115 extends from the hard palate 101 to the hyoid bone (not illustrated). The oropharynx 115 communicates with the nasopharynx 114 superiorly, the oral cavity 111 anteriorly, and the hypopharynx 116 inferiorly.

The tongue 112 is located in the lower portion of the oral cavity 111. The posterior portion of the tongue 112 forms the base of the tongue 113. The epiglottis 105 is a thin structure immediately posterior to the tongue base 113. Although not illustrated, when an individual swallows, the epiglottis 105 covers the entrance of the larynx 107, thereby preventing food or liquids from entering the airway.

As shown in FIG. 1C, the lateral pharyngeal walls 117 (including the palatoglossal and palatopharyngeal arches) form the lateral walls of the oropharynx 115. The palatoglossal arch is a fold of mucosa that runs from the soft palate 102 to the tongue 112. The palatopharyngeal arch is a fold of mucosa posterior to the palatoglossal arch that attaches from the soft palate 102 to the pharyngeal wall. The hypopharynx 116 lies posterior to the larynx 107, extending from the upper border of the epiglottis 105 to the lower border of the cricoid cartilage (not illustrated), and serves as the entrance to the esophagus 106.

FIG. 1A illustrates normal breathing during which the upper airway remains open, allowing air to flow unobstructed. During normal breathing the soft palate 102 naturally falls, the epiglottis 105 opens, and air may enter the trachea 108 via the nasal cavity 110 (or oral cavity 111, during mouth breathing).

FIG. 1B illustrates occurrence of obstructive sleep apnea (OSA) in a patient. When OSA occurs, the soft tissue of the upper airway collapses, and the upper airway is obstructed, resulting in insufficient airflow and even apnea. As illustrated in FIG. 1B, the soft palate 102, the uvula 104, and/or the lateral pharyngeal walls may collapse backwards, causing the passage between soft palate 102 and oropharynx 115 to become narrow or blocked. At the same time, soft tissues of the tongue root 113 may collapse, and the passage between tongue root 113 and soft palate 102 in the oral cavity 111 may become narrow or blocked, resulting in insufficient airflow during breathing and even OSA. In some cases, the collapse of the tongue root 113 not only directly causes the passage between the tongue root 113 and the soft palate 102 to become narrow or blocked, but also causes the passage between the soft palate 102 and the oropharynx 115 to narrow or become blocked.

FIGS. 2A-2I are diagrams illustrating placement of components of a multi-component device used in suspension uvulopalatopexy, consistent with certain exemplary embodiments. Specifically, each of FIGS. 2A through 2I illustrate a multi-component device used to dynamically support and/or retract the soft palate 102, the tongue 112, and/or the lateral pharyngeal walls 117. Generally, the multi-component device includes one or more oral studs inserted into a structure that provides anchoring (e.g., anchor studs 210), one or more oral studs inserted into a structure that are to be supported (e.g., support studs 220), and one or more external elastic connectors 230 that mechanically couple one or more anchor studs 210 to one or more support studs 220. For ease of description, structures that provide anchoring may be referred to herein as anchor or target structures, and structures that are supported by the anchor structures may be referred to herein as support structures. In the disclosed embodiments, support structures may include the soft palate 102, the tongue 112, and/or the lateral pharyngeal walls 117, and anchor structures may include the soft palate 102.

As illustrated in FIGS. 2A-2I, the oral studs (e.g., anchor studs 210 and support studs 220) and elastic connectors 230 may work together to affect a position of the soft palate 102, the tongue 112, and/or the lateral pharyngeal walls 117. For example, the anchor studs 210, support studs 220, and elastic connectors 230 may maintain a position of, or bring forward, the soft palate 102, the tongue 112, and/or the lateral pharyngeal walls 117, thereby maintaining an open passage through the oropharynx 115. At rest, the arrangement of the anchor studs 210 and support studs 220 and the pulling forces applied by each connector 230 may support/displace one or more of the soft palate 102, the tongue 112, and/or the lateral pharyngeal walls 117 in an aerodynamically favorable manner to enhance breathing during sleep while at the same time accommodating the natural movements of these muscular structures during speech, breathing, and swallowing by stretching/contracting passively according to the degree of tension exerted by the contractions of the local musculature.

Figure 2B:
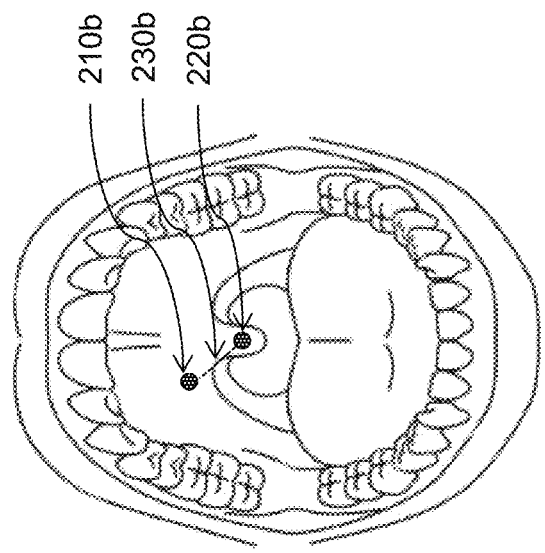
FIGS. 2A-2I are front views of a human mouth illustrating a multi-component device for use in suspension uvulopalatopexy, according to certain exemplary embodiments.
Figure 2A:
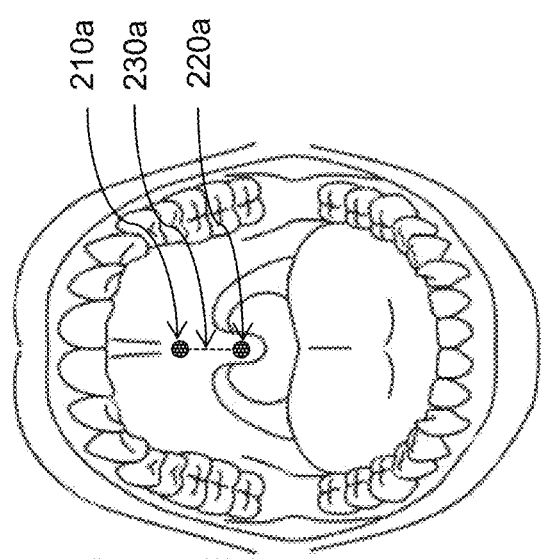

FIG. 2A illustrates an embodiment including two oral studs, i.e., one anchor stud 210a and one support stud 220a. As shown in FIG. 2A, the anchor stud 210a may be inserted through the soft palate 102 at a midline of the soft palate 102, and the support stud 220a may be inserted through another region of the soft palate 102 or the uvula 104. In the embodiment of FIG. 2A, the anchor stud 210a may be inserted at a midline of the soft palate 102, posteriorly to and near the hard palate 101. The anchor stud 210a and the support stud 220a may be connected to one another with a connector 230a external to the palate 103. The connector 230a may extend across the external surface of the palate 103. The connector 230a may be used to alter the position of the uvula 104 and, in particular, move the uvula 104 anteriorly away from the pharynx. In the embodiment illustrated by FIG. 2A, due to the positioning of the anchor stud 210a and the support stud 220a, the uvula 104 may be shifted slightly forward, while maintaining a centered position in the oral cavity 111.

FIG. 2B illustrates an embodiment including two oral studs, i.e., one anchor stud 210b and one support stud 220b. As shown in FIG. 2B, the anchor stud 210b may be inserted through the soft palate 102, and the support stud 220b may be inserted through another region of the soft palate 102 or the uvula 104. In the embodiment of FIG. 2B, the anchor stud 210b may be inserted at a position offset from a midline of the soft palate 102, posteriorly to and near the hard palate 101. The anchor stud 210b and the support stud 220b may be connected to one another with a connector 230b external to the palate 103. The connector 230b may be used to alter the position of the uvula 104 and, in particular, move the uvula 104 anteriorly away from the pharynx. In the embodiment illustrated by FIG. 2B, due to the positioning of the anchor stud 210b and the support stud 220b, the uvula 104 may be shifted forward and slightly off-center in the oral cavity 111.

Figure 2D:
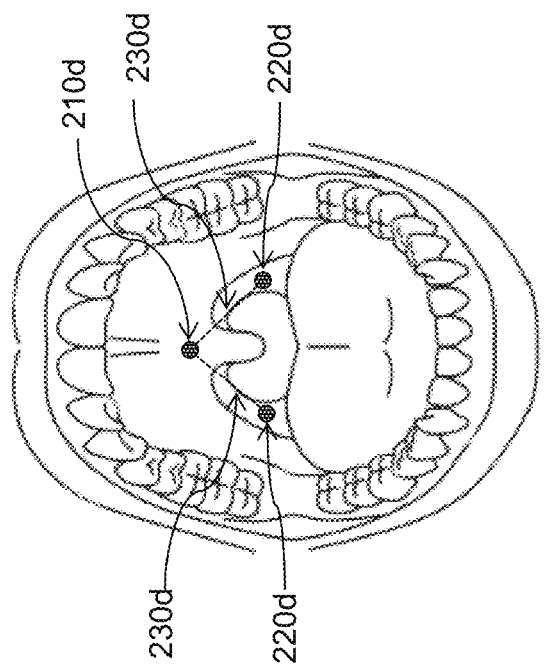
Figure 2C:
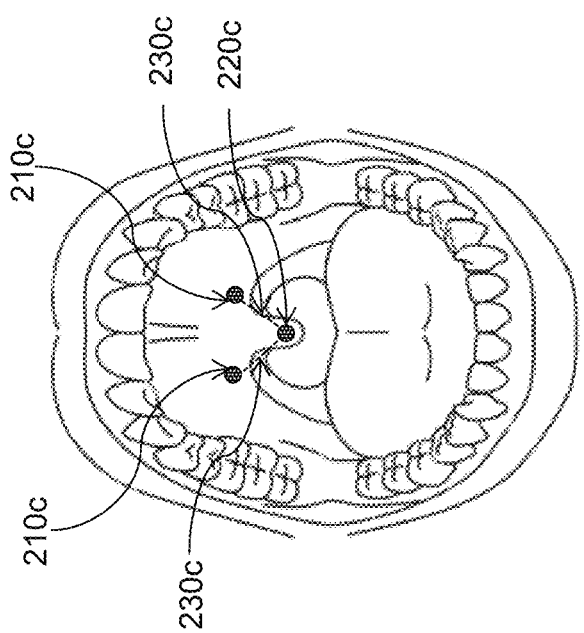

FIG. 2C illustrates an embodiment including three oral studs, i.e., two anchor studs 210c and one support stud 220c. As shown in FIG. 2C, the support stud 220c may be inserted through the uvula 104 at a midline of the uvula 104, and the two anchor studs 210c may be inserted through other regions of the soft palate 102. In the embodiment of FIG. 2C, the anchor studs 210c may be inserted at positions offset from a midline of the soft palate 102, posteriorly to and near the hard palate 101. In some embodiments, the anchor studs 210c may be inserted equidistant from and on opposite sides of the midline of the soft palate 102. The anchor studs 210c and the support stud 220c may be connected with connectors 230c external to the palate 103. For example, a first connector 230c may connect the support stud 220c to a first one of the anchor studs 210c, and a second connector 230c may connect the support stud 220c to a second one of the anchor studs 210c. The connector 230c may be used to alter the position of the uvula 104 and, in particular, move the uvula 104 and/or soft palate 102 anteriorly away from the pharynx. In the embodiment illustrated by FIG. 2C, the uvula 104 may be shifted slightly forward, while maintaining a centered position in the oral cavity 111.

FIG. 2D illustrates an embodiment including three oral studs, i.e., two support studs 220d and one anchor stud 210d. As shown in FIG. 2D, the support studs 220d may be inserted through the lateral pharyngeal walls 117, with one on either side of the soft palate 102, and the one anchor stud 210d may be inserted through an upper region of the soft palate 102. In the embodiment of FIG. 2D, the anchor stud 210d may be inserted at a midline of the soft palate 102, posteriorly to and near the hard palate 101. The anchor stud 210d and the support studs 220d may be connected to one another with connectors 230d external to the palate 103. For example, a first connector 230d may connect the anchor stud 210d to a first one of the support studs 220d, and a second connector 230d may connect the anchor stud 210d to a second one of the support studs 220d. The connectors 230d may be used to alter the position of the lateral pharyngeal walls 117 and, in particular, move the lateral pharyngeal walls 117 anteriorly away from the pharynx. In the embodiment illustrated by FIG. 2D, the lateral pharyngeal walls 117 may be shifted slightly forward in the oral cavity 111.

Figure 2F:
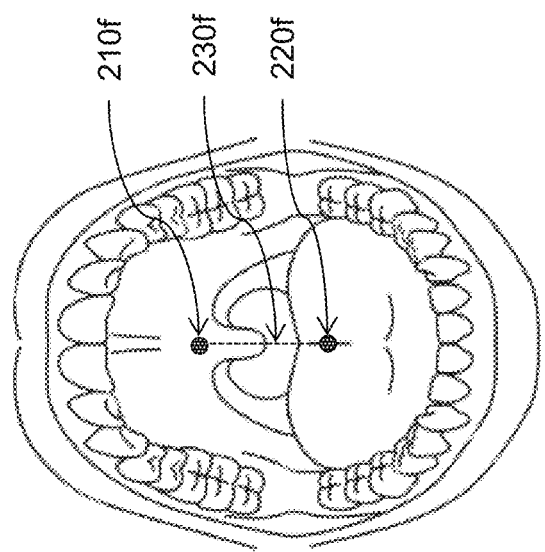
Figure 2E:
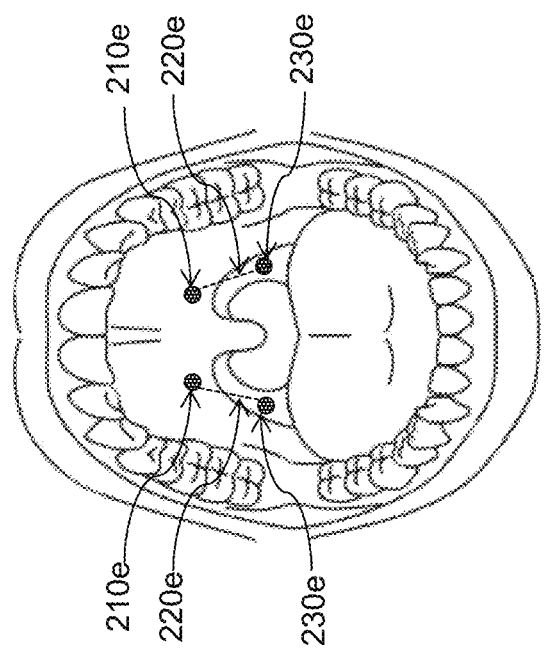

FIG. 2E illustrates an embodiment including four oral studs, i.e., two anchor studs 210e and two support studs 220e. As shown in FIG. 2E, the support studs 220e may be inserted through the lateral pharyngeal walls 117, with one on either side of the soft palate 102, and the two anchor studs 210e may be inserted through an upper region of the soft palate 102. In the embodiment of FIG. 2E, the anchor studs 210e may be inserted at positions offset from a midline of the soft palate 102, posteriorly to and near the hard palate 101. In some embodiments, the anchor studs 210e may be inserted equidistant from and on opposite sides of the midline of the soft palate 102. The anchor studs 210e and the support studs 220e may be connected to one another with connectors 230e external to the palate 103. For example, a first connector 230e may connect a first one of the support studs 220e to a first one of the anchor studs 210e, and a second connector 230e may connect a second one of the support studs 220e to a second one of the anchor studs 210e. The connectors 230e may be used to alter the position of the lateral pharyngeal walls 117 and, in particular, move the lateral pharyngeal walls 117 anteriorly away from the pharynx. In the embodiment illustrated by FIG. 2E, the lateral pharyngeal walls 117 may be shifted slightly forward in the oral cavity 111.

FIG. 2F illustrates an embodiment including two oral studs, i.e., one anchor stud 210f and one support stud 220f. As shown in FIG. 2F, the support stud 220f may be inserted through the tongue 112 or tongue root 113, and the anchor stud 210f may be inserted through an upper region of the soft palate 102. The support stud 220f may be inserted at a midline position of the tongue 112 or tongue root 113. In the embodiment of FIG. 2F, the anchor stud 210f may be inserted at a midline position of the soft palate 102, posteriorly to and near the hard palate 101. The anchor stud 210f and the support stud 220f may be connected to one another with connector 230f external to the palate 103. The connector 230f may be used to alter the position of the tongue 112 and, in particular, move the tongue 112 anteriorly away from the pharynx. In the embodiment illustrated by FIG. 2F, the tongue 112 may be shifted slightly forward in the oral cavity 111.

Figure 2H:
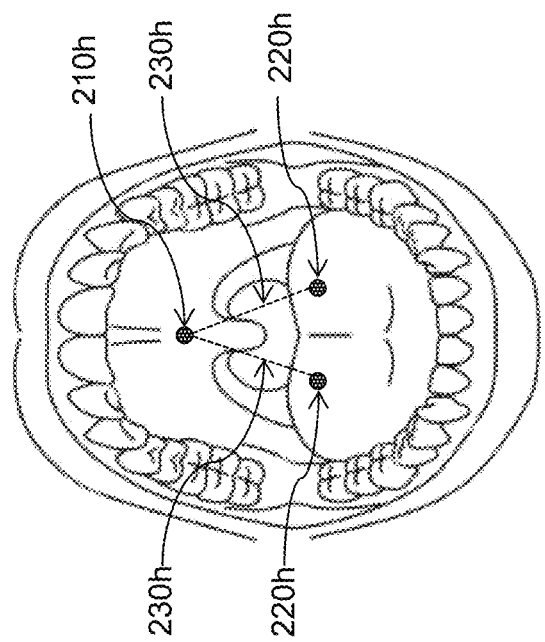
Figure 2G:
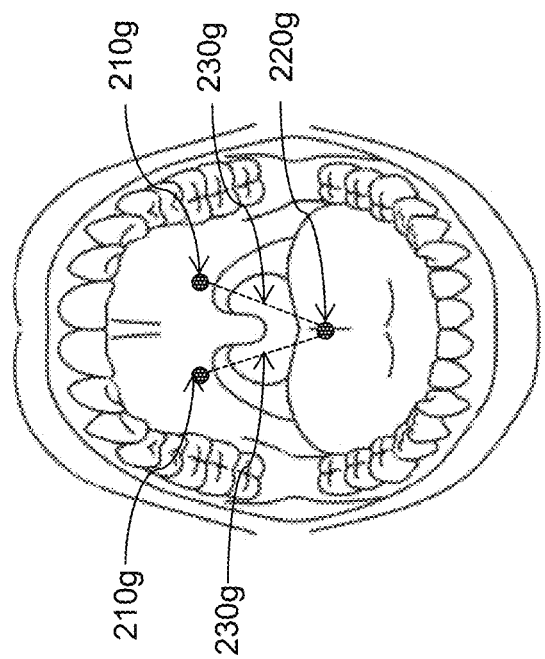

FIG. 2G illustrates an embodiment including three oral studs, i.e., one support stud 220g and two anchor studs 210g. As shown in FIG. 2G, the support stud 220g may be inserted through the tongue 112 or tongue root 113, and the two anchor studs 210g may be inserted through an upper region of the soft palate 102. The support stud 220g may be inserted at a midline position of the tongue 112 or tongue root 113. In the embodiment of FIG. 2G, the anchor studs 210g may be inserted at positions offset from a midline of the soft palate 102, posteriorly to and near the hard palate 101. In some embodiments, the anchor studs 210g may be inserted equidistant from and on opposite sides of the midline of the soft palate 102. The support studs 220g and the anchor studs 210g may be connected to one another with connectors 230g external to the palate 103. For example, a first connector 230g may connect the support stud 220g to a first one of the anchor studs 210g, and a second connector 230g may connect the support stud 220g to a second one of the anchor studs 210g. The connectors 230g may be used to alter the position of the tongue 112 and, in particular, move the tongue 112 anteriorly away from the pharynx. In the embodiment illustrated by FIG. 2G, the tongue 112 may be shifted slightly forward in the oral cavity 111.

FIG. 2H illustrates an embodiment including three oral studs, i.e., two support studs 220h and one anchor stud 210h. As shown in FIG. 2H, the support studs 220h may be inserted through the tongue 112 or tongue root 113, with one on either side of a midline of the tongue 112, and the anchor stud 210h may be inserted through an upper region of the soft palate 102. In the embodiment of FIG. 2H, the anchor stud 210h may be inserted at a midline of the soft palate 102, posteriorly to and near the hard palate 101. The support studs 220h and the anchor stud 210h may be connected to one another with connectors 230h external to the palate 103. For example, a first connector 230h may connect a first one of the support studs 220h to the anchor stud 210h, and a second connector 230h may connect a second one of the support studs 220h to the anchor stud 210h. The connectors 230h may be used to alter the position of the tongue 112 and, in particular, move the tongue 112 anteriorly away from the pharynx. In the embodiment illustrated by FIG. 2H, the tongue 112 may be shifted slightly forward in the oral cavity 111.

Figure 2I:
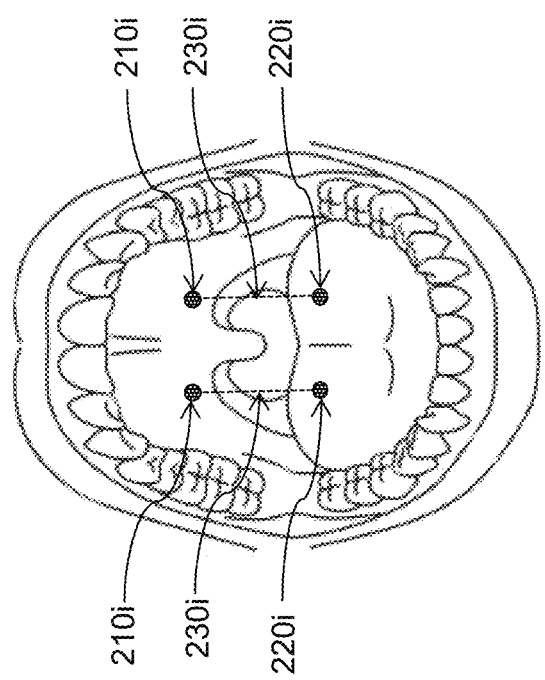

FIG. 2I illustrates an embodiment including four oral studs, i.e., two anchor studs 210i and two support studs 220i. As shown in FIG. 2I, the support studs 220i may be inserted through the tongue 112 or tongue root 113, with one on either side of a midline of the tongue 112, and the two anchor studs 210i may be inserted through an upper region of the soft palate 102. In the embodiment of FIG. 2I, the anchor studs 210i may be inserted at positions offset from a midline of the soft palate 102, posteriorly to and near the hard palate 101. In some embodiments, the anchor studs 210i may be inserted equidistant from and on opposite sides of the midline of the soft palate 102. The anchor studs 210i and the support studs 220i may be connected to one another with connectors 230i external to the palate 103. For example, a first connector 230i may connect a first one of the support studs 220i to a first one of the anchor studs 210i, and a second connector 230i may connect a second one of the support studs 220i to a second one of the anchor studs 210i. The connectors 230i may be used to alter the position of the tongue 112 and, in particular, move the tongue 112 anteriorly away from the pharynx. In the embodiment illustrated by FIG. 2I, the tongue 112 may be shifted slightly forward in the oral cavity 111.

Figure 3B:
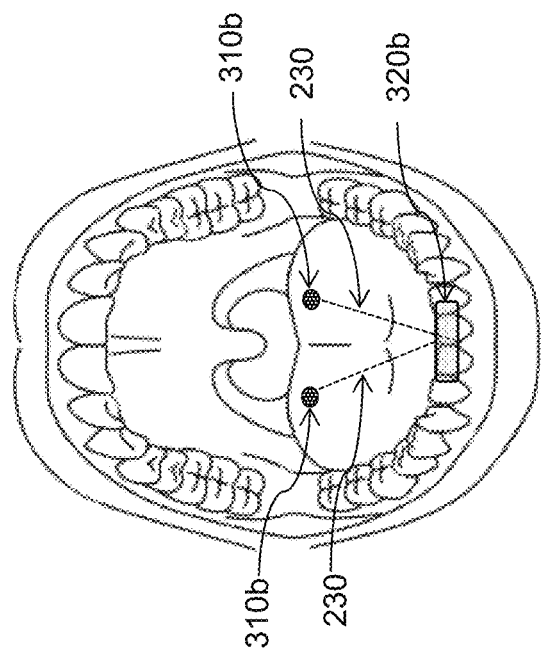
FIGS. 3A-3B are front views of a human mouth illustrating a multi-component device for use in suspension glossomandibulopexy, according to certain exemplary embodiments.
Figure 3A:
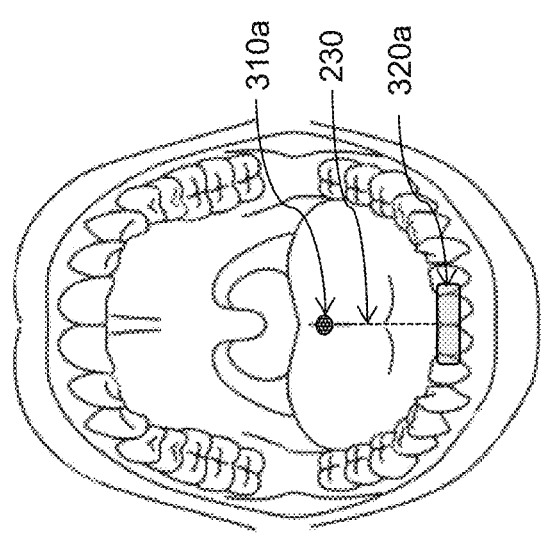

FIGS. 3A-3B are front views of a human head to illustrate placement of components of a multi-component device used in suspension glossomandibulopexy, consistent with certain exemplary embodiments. Specifically, FIGS. 3A-3B illustrate an embodiment in which an oral stud 310 is inserted into the tongue 112, bringing the tongue 112 forward in the oral cavity 111 and increasing the space in the oropharynx 115. In the embodiments illustrated by FIGS. 3A-3B, the multi-component device includes at least one oral stud 310 inserted into a tongue 112, a dental anchor 320 attached to or inserted into a structure that provides support, and one or more external elastic connectors 230 that mechanically couple the at least one oral stud 310 to the dental anchor 320. The oral stud 310 may correspond to the anchor studs 210, discussed above in connection with FIGS. 2A-2I. As illustrated in FIGS. 3A-3B, the oral stud 310, dental anchor 320, and elastic connector 230 may maintain a position of, or bring forward, the tongue 112 in the oral cavity 111, thereby maintaining an open passage through the oropharynx 115.

FIG. 3A illustrates an embodiment including one oral stud 310a and a dental anchor 320a. As shown in FIG. 3A, the oral stud 310a may be inserted through the tongue 112 or tongue root 113 at a midline position of the tongue 112 or tongue root 113. In the embodiment of FIG. 3A, the dental anchor 320a may be removably attached to a patient's teeth (e.g., placed over the patient's teeth), such that the patient's teeth hold the dental anchor 320a firmly in place. In this manner, the dental anchor 320a may be inserted and/or removed from the patient's oral cavity 111, as desired. The oral stud 310a and the dental anchor 320a may be connected to one another with a connector 230 external to the tissue of the tongue 112 or tongue root 113. The connector 230 may be used to alter the position of the tongue 112 and, in particular, move the tongue 112 anteriorly away from the oropharynx 115. In the embodiment illustrated by FIG. 3A, the tongue 112 may be shifted slightly forward in the oral cavity 111.

FIG. 3B illustrates an embodiment including two oral studs 310b and a dental anchor 320a. As shown in FIG. 3B, the oral studs 310b may be inserted through the tongue 112 or tongue root 113, with one on either side of a midline of the tongue 112 or tongue root 113. In the embodiment of FIG. 3B, the dental anchor 320b may be removably attached to a patient's teeth (e.g., placed over the patient's teeth), such that the patient's teeth hold the dental anchor 320b firmly in place. In this manner, the dental anchor 320b may be inserted and/or removed from the patient's oral cavity 111, as desired. The oral studs 310b and the dental anchor 320b may be connected to one another with connectors 230 external to the tissue of the tongue 112 or tongue root 113. The connectors 230 may be used to alter the position of the tongue 112 and, in particular, move the tongue 112 anteriorly away from the oropharynx 115. In the embodiment illustrated by FIG. 3B, the tongue 112 may be shifted slightly forward in the oral cavity 111.

The embodiments of FIGS. 2A-2I and 3A-3B may support/displace the soft palate 102, the tongue 112, and/or the lateral pharyngeal walls 117, thereby improving breathing while causing minimal interference with speech, breathing, and swallowing. In addition, one or more of the size, location, and number of oral studs, as well as the number, type, and tension-grade of the elastic connectors may be altered to introduce flexibility in the customization to the individual patient, thereby maximizing the likelihood for compliance and efficacy in patients suffering from OSA, upper airway resistance syndrome (UARS), and snoring. A single stud or multiple studs may also be used as cosmetic piercings (and need not be used for snoring/sleep apnea).

Figure 4A:
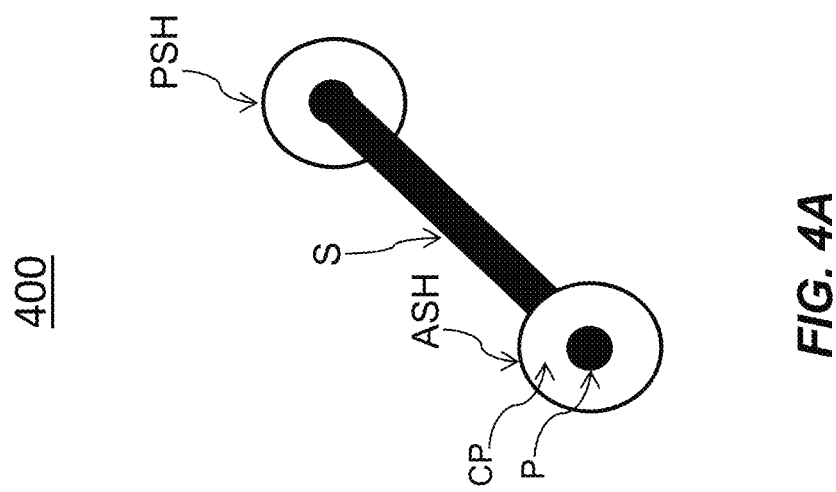
Figure 4C:
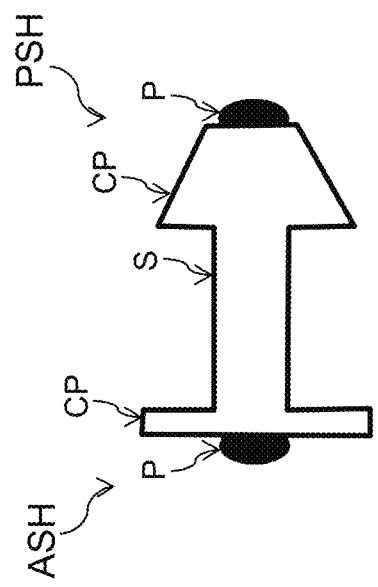

FIGS. 4A and 4B are schematics illustrating an oral stud 400, according to certain exemplary embodiments. As discussed above, the oral stud 400 may be an anchor stud 210 or a support stud 220. FIG. 4A illustrates a perspective view of an oral stud 400, FIG. 4B illustrates a side view of an oral stud 400, and FIG. 4C illustrates a side view of an oral stud 400.

The oral stud 400 may include a shaft S, a posterior stud head PSH, and an anterior stud head ASH. In some examples, the oral stud 400 may be formed as a single contiguous integrated piece of the same material, such as a flexible plastic material. The shaft S may consist of a rigid material or semi-rigid material (e.g., a suture). The posterior stud head PSH and the anterior stud head ASH may be located at opposite ends of the shaft S. The posterior stud head PSH may be the end of the oral stud 400 that is inserted through the support site (e.g., the uvula 104, the tongue 112, and/or the lateral pharyngeal walls 117) or the anchor site (e.g., the soft palate 102). The anterior stud head ASH may be the end of the oral stud 400 that is located inside the oral cavity 111. In some embodiments, the posterior stud head PSH and the anterior stud head ASH may include circular plates CP that uniformly extend perpendicularly away from the shaft S.

The circular plate CP of each of the posterior stud head PSH and the anterior stud head ASH may have a first side that has a flat or planar shape. The first side may be the side of the circular plate CP nearest the shaft S. For example, the first side may be on the side adjacent to the tissue through which the oral stud 400 is to be inserted. The circular plate CP may have a diameter $D_{CP}$ and a thickness $T_{CP}$. The diameter $D_{CP}$ of the circular plate CP may be in the range of, for example, several millimeters (e.g., 2-7 millimeters, or more particularly, 3-5 millimeters), and the thickness $T_{CP}$ of the circular plate CP may be in the range of, for example, one or more millimeters (e.g., 1-7 millimeters, or more particularly, 2-3 millimeters). The diameter $D_{CP}$ of the circular plate CP may be larger than a diameter $D_S$ of the shaft S. Although the posterior stud head PSH and the anterior stud head ASH are described as plates having a circular shape, it is envisioned that the plates may be formed to have other shapes (e.g., square, rectangular, triangular, pentagonal, etc.). In some cases, the shape of the plates may be determined based on the placement location. For example, a rectangular plate may be used for locations that are narrower or have an elongated shape (e.g., the lateral pharyngeal walls 117).

The shaft S may be the portion of the oral stud 400 that is located within tissue of the target (anchor) site and/or the support site. For example, when the oral stud 400 is inserted through the uvula 102, the posterior stud head PSH may be located external to the uvula 104 in the nasopharynx 114, the anterior stud head ASH may be located external to the uvula 104 in the oral cavity 111, and the shaft S may extend through the tissue of the uvula 102 between the oral cavity 111 and the nasopharynx 114. As another example, when the oral stud 400 is inserted through the soft palate 102, the posterior stud head PSH may be located external to the soft palate 102 in the nasopharynx 114, the anterior stud head ASH may be located external to the soft palate 102 in the oral cavity 111, and the shaft S may extend through the tissue of the soft palate 102 between the oral cavity 111 and the nasopharynx 114. As a further example, when the oral stud 400 is inserted through the lateral pharyngeal walls 117, the posterior stud head PSH may be located external to the lateral pharyngeal walls 117 in the oropharynx 115, the anterior stud head ASH may be located external to the lateral pharyngeal walls 117 in the oral cavity 111, and the shaft S may extend through the interior of the lateral pharyngeal walls 117 between the oral cavity 111 and the oropharynx 115.

The shaft S may have a length Ls corresponding to the length of the hole created in the target (anchor) or support site. For example, the length Ls of the shaft S may be such that the shaft S is almost entirely contained within tissue of the target (anchor) or support site. A length Ls of the shaft S may correspond to a thickness of the region into which the shaft S is inserted, and may be in the range of, for example, several millimeters to several centimeters. In some embodiments, the length of the shaft S may be 1-2 millimeters longer than the thickness of the region into which the shaft S is inserted. The shaft S may be a cylinder shape and have a diameter $D_S$ in the range of, for example, one or more millimeters (e.g., 1-7 millimeters, or more particularly, 2-3 millimeters). The diameter $D_S$ of the shaft S may be proportional to its length Ls. For example, a shaft S having a greater length Ls may also have a larger diameter $D_S$, whereas a shaft S having a shorter length Ls may have a smaller diameter $D_S$. In addition, a diameter $D_S$ of the shaft S may be determined such that the shaft S, while maintaining flexibility, does not distend or stretch to a greater length.

As shown in FIGS. 4B and 4C, in some embodiments, the posterior stud head PSH may include a plate that is collapsible in one direction (e.g., collapsing toward the central axis of the shaft S and toward the body of the stud, such as away from the insertion direction) to facilitate insertion through the target (anchor) or support site, but resists collapsing in the other direction (e.g., does not collapse toward the axis of the stud away from the body of the stud, such as towards the insertion direction) so that the plate spreads in an uncollapsed position against the surface of the target (anchor) or support site to prevent the oral stud 400 from being extracted through the hole in the target (anchor) or support site, thus keeping the oral stud 400 in place. In FIG. 4B, the circular plate CP may have a rectangular shape, when viewed from the side, whereas in FIG. 4C, the circular plate CP have a trapezoidal shape (e.g., an isosceles trapezoidal shape), when viewed from the side.

The oral stud 400 may be made of a biocompatible material suitable for long-term implantation within the human body, such as, for example, a metal (e.g., stainless steel, cobalt alloys, titanium alloys, etc.), a ceramic (e.g., aluminum oxide, zirconia, calcium phosphates, etc.), synthetic polymers (e.g., nylon, silicones, poly (ethylene), poly (vinyl chloride), polyurethanes, polylactides, etc.), natural polymers (e.g., collagen, gelatin, elastin, silk, polysaccharide, etc.), or any combination thereof. The oral stud 400 may be formed of shape memory materials (SMMs), which are featured by their ability to recover their original shape from a significant and seemingly plastic deformation when a particular stimulus is applied (e.g., superelasticity, viscoelasticity). The ability to return to their original shape is known as the shape memory effect.

In certain embodiments, the oral stud 400 may be comprised of a silicone or plastic material. When made of silicone or plastic, the oral stud is lightweight to help avoid irritation. The light weight also may help in allowing the oral stud 400 to be expelled (by coughing, e.g.) in the event it is dislodged and falls into the airway. The oral stud 400 may also be easily removed (e.g., by clipping the shaft S) in the event the oral stud 400 becomes uncomfortable or the patient's tissue becomes irritated or infected. The thickness and/or material strength of the shaft S may be such that the shaft S may be cut by hand, using a hand-held, mechanical device (e.g., clippers). The material of the shaft S may consist of a rigid material or a semi-rigid material (e.g., a suture).

FIGS. 5A and 5B are schematics illustrating oral studs 400 with blades 502 extending through a central axis, according to exemplary embodiments. In some embodiments, the oral stud 400 may include a passageway along a central axis of the shaft S, extending from the posterior stud head PSH to the anterior stud head ASH. The passageway may allow for extension and retraction of a blade 502 along the hollow center. In some embodiments, the passageway may correspond to the size and shape of the blade 502. The blade 502 may be used to pierce the target (anchor) and/or support site, thereby allowing insertion and placement of an oral stud 400.

FIG. 5A is a front view of an oral stud 400 with the blade 502 fully extended through the oral stud 400, and FIG. 5B is a side view of the oral stud 400 with the blade 502 fully extended along the central passageway of the oral stud 400. As shown in the embodiments of FIGS. 5A and 5B, both the height $H_B$ and the width $W_B$ of the blade 502 may be smaller than the diameter $D_P$ of the projection P and the diameter $D_S$ of the shaft S. The height $H_B$ and the width $W_B$ of the blade 502 may be the same as or different from one another. Although not illustrated, in some embodiments, the $H_B$ and the width $W_B$ of the blade 502 may be the same and may correspond to a diameter of the blade 502.

Figure 6B:
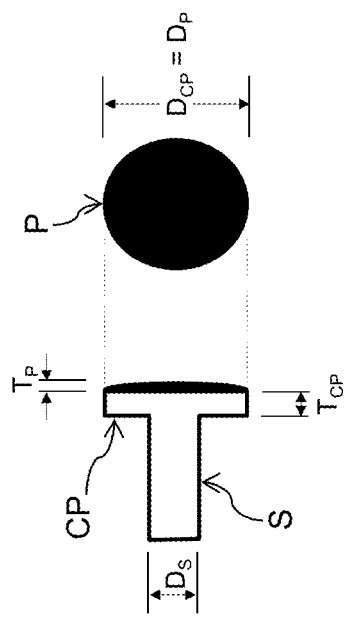
FIGS. 6A-6G are schematics of alternative stud heads of an oral stud, according to certain exemplary embodiments.
Figure 6A:
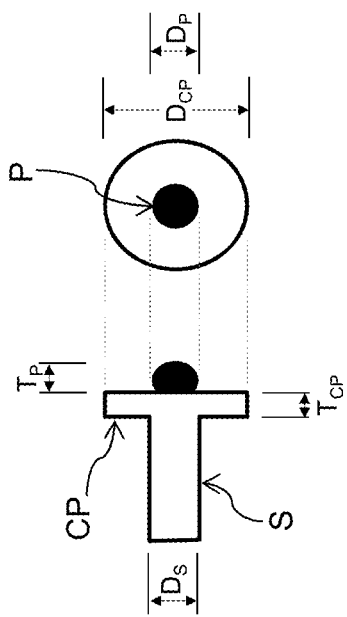
Figure 6C:
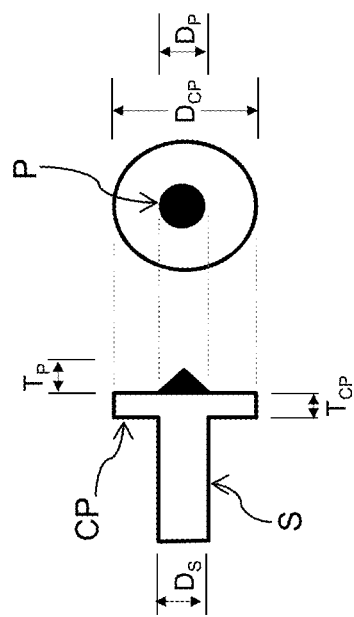
Figure 6D:
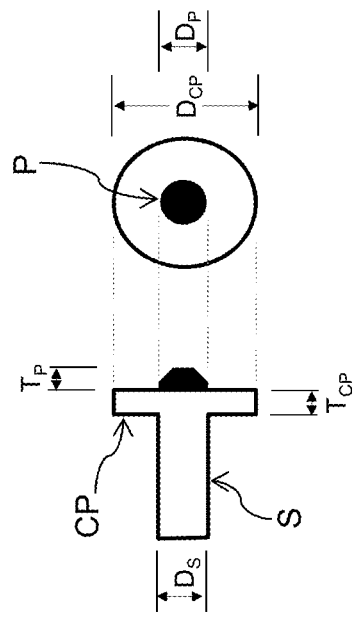
Figure 6E:
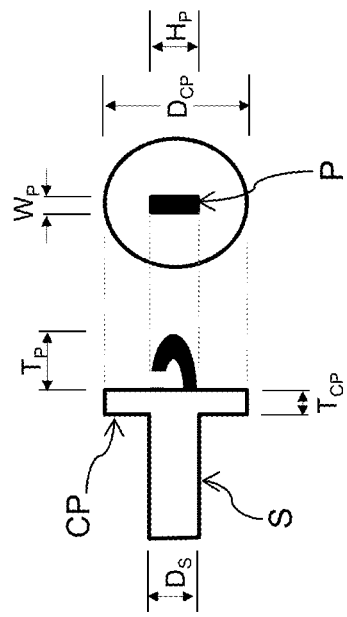
Figure 6F:
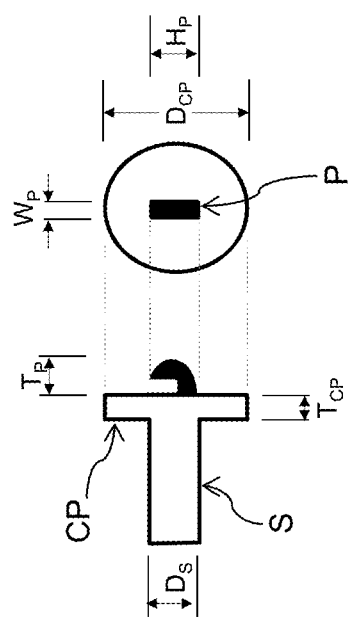
Figure 6G:
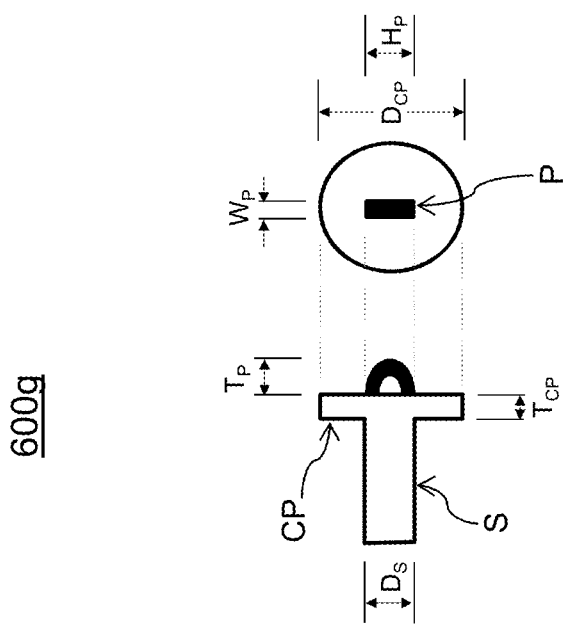

FIGS. 6A-6G are schematics illustrating stud heads 600a through 600g, respectively, according to certain exemplary embodiments. The stud heads 600a through 600g may correspond to the posterior stud head PSH and/or the anterior stud head ASH of FIGS. 5A and 5B above. In the embodiments of FIGS. 6A-6G, each of the stud heads 600a through 600g may include a circular plate CP having a first side that has a flat or planar shape. The first side may be the side of the circular plate CP nearest the shaft S. Each of the stud heads 600a through 600g may have a second side, opposite to the first side and facing away from the shaft S, that includes a projection P. The projection P may be formed on a top surface of the second side of the circular plate CP to project in a direction away from the shaft S. As illustrated in FIGS. 6A-6G, the projection P may have a variety of shapes, such as, for example, a knob shape (FIG. 6A), a bump shape (FIG. 6B), a sharp or pointed pyramidal shape (FIG. 6C), a rounded pyramidal shape (FIG. 6D), a rounded notched shape (FIG. 6E), a hook shape (FIG. 6F), or a loop shape (FIG. 6G).

When the shape of the projection P, when viewed face-on, is rounded (e.g., FIGS. 6A-6G), the projection P may have a diameter $D_P$ and a thickness $T_P$. The diameter $D_P$ of the projection P may be in the range of, for example, one or more millimeters (e.g., 1-7 millimeters, or more particularly, 2-3 millimeters), and the thickness $T_P$ of the projection P may be in the range of, for example, one or more millimeters (e.g., 1-7 millimeters, or more particularly, 2-3 millimeters). In some embodiments, the diameter $D_P$ of the projection P may be the same as or different from a diameter $D_S$ of the shaft S. For example, in the embodiments of FIGS. 6A, 6C, 6D, and 6E, the diameters $D_P$ of the projections P are the same as the diameters $D_S$ of the respective shafts S. In the embodiment of FIG. 6B, the diameter $D_P$ of the projection P may be larger than the diameter $D_S$ of the shaft S, and may be the same as the diameter Du of the circular plate CP.

When the shape of the projection, when viewed face-on, is irregular (e.g., FIG. 6F or FIG. 6G), the projection P may have a height $H_P$, a width $W_P$, and a thickness $T_P$. The height $H_P$ of the projection P may be in the range of, for example, one or more millimeters (e.g., 1-7 millimeters, or more particularly, 2-3 millimeters), the width $W_P$ of the projection P may be in the range of, for example, one or more millimeters (e.g., 1-7 millimeters, or more particularly, 2-3 millimeters), and the thickness $T_P$ of the projection P may be in the range of, for example, one or more millimeters (e.g., 1-7 millimeters, or more particularly, 2-3 millimeters). In some embodiments, the height $H_P$ and/or width $W_P$ of the projection P may be the same as or different from a diameter $D_S$ of the shaft S. For example, in the embodiments of FIGS. 6F and 6G, the height $H_P$ of the projection P is the same as the diameter $D_S$ of the shaft S and the width $W_P$ of the projection P is smaller than the diameter $D_S$ of the shaft S. Further, although not illustrated, when the shape of the projection is irregular, when the blade 502 is extended through the oral stud 400, the projection P may be shifted or tilted to a side, as discussed in more detail below.

In some embodiments, the posterior stud head PSH and the anterior stud head ASH connected to a same shaft S may include projections P having a same or different material, shape, thickness $T_P$, height $H_P$, width $W_P$, and/or diameter $D_P$. In some embodiments, for example, the posterior stud head PSH may have a smaller thickness $T_P$ and larger diameter $D_P$ than those of the anterior stud head ASH located at the opposite end of the shaft S. The material, shape, thickness $T_P$ and/or diameter $D_P$ of the projection P may be determined based on the insertion location or the needs of the patient, and whether the projection P is located on the anterior stud head ASH or the posterior stud head PSH. For example, referring to the embodiment of FIG. 6E, the projection P may have a rounded shape with a notch to retain one end of the connector 230, in the embodiment of FIG. 6F, the projection P may have a hook shape to retain one end of the connector 230, and in the embodiment of FIG. 6G, the projection P may have a loop shape including an opening to retain one end of connector 230. In some exemplary embodiments, the projections P illustrated in FIGS. 6E-6G may be located on the anterior stud heads ASH of the oral stud 400.

In some embodiments, one or more of the projections P of the posterior stud head PSH and/or the anterior stud head ASH may be augmented with additional materials or may be comprised of different materials. For example, in some embodiments, the projection P of the posterior stud head PSH, such as those of FIGS. 6E and 6F, may have a biocompatible metal contained within, and surrounded by, the elastic material forming the oral stud 400. By including a metal in this manner, the projection P may have added rigidity, thereby increasing the ability of the projection P to retain a connector 230.

In other embodiments, the projection P may be formed of a metal, such that an end of the connector 230 is retained against the projection P through a magnetic force. For example, in such an embodiment, the projection P may be a rounded shape (e.g., projection P in FIG. 5A), and the connector may be a cup-shaped magnet or magnetized material that retains and at least partially surrounds the projection P.

The diameter $D_S$ and length Ls of the shaft S, as well as the thicknesses and diameters of features of the posterior stud head PSH and the anterior stud head ASH, may be determined based on a combination of one or more of the following: (1) the physical size and shape of the target (anchor) and/or support sites and the patient's anatomy, (2) a number of the oral studs, (3) an insertion location of the oral studs, and (4) a desired treatment plan or protocol. For example, when only a smaller displacement force is desired, a fewer number of oral studs may be used and/or the oral studs may be smaller in size, and when a larger displacement force is desired, a larger number of oral studs may be used and/or the oral studs may be larger in size. As another example, the $D_S$ and/or length Ls of the shaft S may be based on parameters of the patient's anatomy and/or treatment protocol. For example, a desired diameter $D_S$ and/or length of the shaft S may be determined based on one or more of a desired amount of tension, an amount of collapse of tissue, a thickness and/or volume of the physical structure to be supported or the physical structure providing the support, patient comfort and/or tolerance, etc.

When fully deployed, a size or contact area of the posterior stud head PSH and/or the anterior stud head ASH may be determined so as to distribute force along a greater area of the patient's tissue. For example, with a greater contact area (e.g., the area of the circular plate CP), the pulling forces at a target (anchor) site and/or the support site (e.g., uvula 104, tongue 112, and/or lateral pharyngeal walls 117) may be dispersed across a greater surface area, thereby reducing irritation and/or discomfort to the patient. The posterior stud head PSH and the anterior stud head ASH may have the same or different shapes and sizes. In some embodiments, the posterior stud head PSH and the anterior stud head ASH may have circular plate CP with the same diameter $D_{CP}$ and thickness $T_{CP}$, but a different shaped projection P. For example, the posterior stud head PSH may have a projection P with a rounded knob shape as in FIG. 6A, and the anterior stud head ASH may have a projection with a rounded notched shape as in FIG. 6E. As another example, the posterior stud head PSH may have a projection P with a bump shape as in FIG. 6B, and the anterior stud head ASH may have a projection with a looped shape as in FIG. 6G.

FIGS. 7A-7D are schematics illustrating exemplary connectors 230, according to certain embodiments. Connectors 230 may be made of a biocompatible material, such as, for example, metal (e.g., stainless steel, cobalt alloys, titanium alloys, etc.), a ceramic (e.g., aluminum oxide, zirconia, calcium phosphates, etc.), synthetic polymers (e.g., nylon, silicones, poly (ethylene), poly (vinyl chloride), polyurethanes, polylactides, etc.), natural polymers (e.g., collagen, gelatin, elastin, silk, polysaccharide, etc.), or any combination thereof. The connectors 230 may include a shape memory material (SMM), such that the connector 230 is able to maintain and/or recover its original shape from a significant and seemingly plastic deformation when a particular stimulus is applied (e.g., superelasticity, visco-elasticity). For example, in each of the embodiments of FIGS. 7A-7D, connector 230 may be formed of a material having superelasticity, such that the force of the connector 230 returning to its original shape causes a gentle, continuous pressure to be applied to the anchor studs 210 and support studs 220 to which it is connected.

Figure 7B:
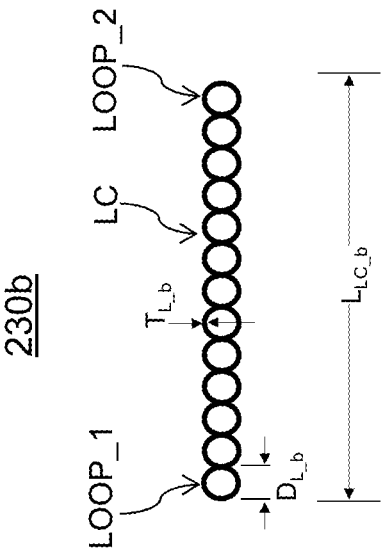
FIG. 7A-7D are diagrams illustrating connectors for connecting oral studs, according to certain exemplary embodiments.
Figure 7A:
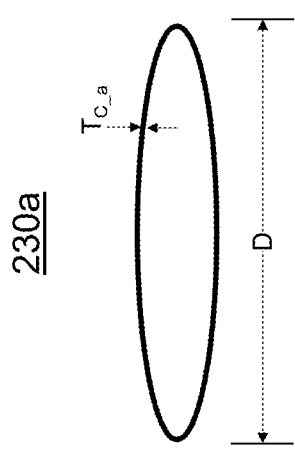

In the embodiment of FIG. 7A, connector 230a may be a single continuous loop formed from an elastic band. The continuous loop that forms the connector 230a may attach to an anchor stud 210 and/or a support stud 220 via anterior stud heads ASH having a shape that retains the connector 230a (see, e.g., embodiments of FIGS. 6E and 6F). Connector 230a may be formed of an elastic material that applies a gentle pressure to the anchor stud 210 and support stud 220 to which it is connected. The elastic band that forms the connector 230a may have a thickness $T_{C\_a}$ of, for example, approximately one or more millimeters (e.g., 1-7 millimeters, or more particularly, 2-3 millimeters), and a circumferential length $CL_{C\_a}$ of, for example, many millimeters (e.g., 10-200 millimeters, or more particularly, 100-150 millimeters). The thickness $T_{C\_a}$ and/or the circumferential length $CL_{C\_a}$ of the connector 230a may be determined based on a distance between the anchor stud 210 and the support stud 220 to which it is connected, as well as an amount of pressure that is to be applied to the anchor stud 210 and the support stud 220, and an elasticity of the material forming the connector 230a.

In the embodiment of FIG. 7B, connector 230b may be a series of small interconnected loops, and may be comprised of an elastic or rubber material. A first loop LOOP_1 of the series of loops that form the connector 230b may attach to an anchor stud 210 having a shape that retains the connector 230b (see, e.g., embodiments of FIGS. 6E and 6F), and a second loop LOOP_2 may attach to a support stud 220 having a shape that retains the connector 230b (see, e.g., embodiments of FIGS. 6E and 6F). There may be one or more third loops located between the first loop LOOP_1 and the second loop LOOP_2. The number of third loops may correspond to a length component LC of the connector 230b, where the length $L_{LC\_b}$ of the connector 230b is the end-to-end length of the connector 230b when it is not extended. The material that forms the connector 230 may have a thickness $T_{L\_b}$ of, for example, approximately one or more millimeters (e.g., 1-7 millimeters, or more particularly, 2-3 millimeters), and each loop may have a diameter $D_{L\_b}$ of, for example, several millimeters (e.g., 3-7 millimeters, or more particularly, 4-5 millimeters). The thickness $T_{L\_b}$, the loop diameter $D_{L\_b}$, and/or the number of loops of the connector 230b may be determined based on a distance between the anchor stud 210 and the support stud 220 to which it is connected, as well as an amount of pressure that is to be applied to the anchor stud 210 and the support stud 220, and an elasticity of the material forming the connector 230b.

Figure 7D:
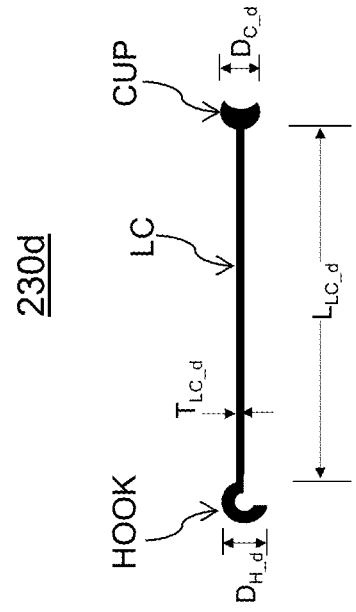
Figure 7C:
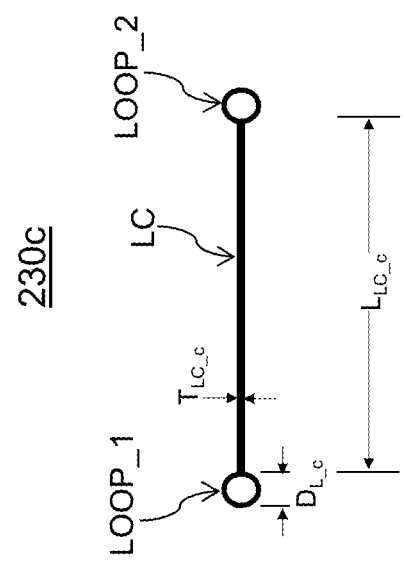

In the embodiment of FIG. 7C, connector 230c may consist of two loops LOOP_1 and LOOP_2, connected with one another by a linear component LC. The two loops LOOP_1 and LOOP_2 and the linear component LC may be comprised of an elastic or rubber material. One loop LOOP_1 of the connector 230c may attach to an anchor stud 210 having a shape that retains the connector 230c (see, e.g., embodiments of FIGS. 6E and 6F), and a second loop LOOP_2 of the connector 230c may attach to a support stud 220 having a shape that retains the connector 230c (see, e.g., embodiments of FIGS. 6E and 6F). The linear component LC may attach the first loop LOOP_1 to the second LOOP_2, and may have a length $L_{LC\_c}$ measured from the first loop LOOP_1 to the second LOOP_2. The length $L_{LC\_c}$ of the linear component LC may be in the range of, for example, several millimeters (e.g., 25-300 millimeters, or more particularly, 50-125 millimeters). The material that forms the connector 230 may have a thickness $T_{LC\_c}$ of, for example, one or more millimeters (e.g., 1-7 millimeters, or more particularly, 2-3 millimeters), and each loop may have a diameter $D_{L\_c}$ of, for example, several millimeters (e.g., 3-7 millimeters, or more particularly, 4-5 millimeters). The thickness $T_{LC\_c}$, the loop diameter $D_{L\_c}$, and/or the length $L_{LC\_c}$ of the linear component LC of the connector 230c may be determined based on a distance between the anchor stud 210 and the support stud 220 to which it is connected, as well as an amount of pressure that is to be applied to the anchor stud 210 and the support stud 220, and an elasticity of the material forming the connector 230c.

In the embodiment of FIG. 7D, connector 230d may consist of a cup CUP and a hook HOOK, connected with one another by a linear component LC. The cup CUP and a hook HOOK may be comprised of a first rigid material (e.g., a metal), and the linear component LC may be comprised of an elastic material. The cup CUP of the connector 230d may attach to an anchor stud 210 having a shape that fits within the cup CUP (see, e.g., embodiment of FIG. 6A), and the hook HOOK of the connector 230d may attach to a support stud 220 having a shape that retains the connector 230d (see, e.g., embodiments of FIG. 6G). The linear component LC may attach the cup CUP to the hook HOOK, and may have a length $L_{LC\_d}$ measured from the cup CUP to the hook HOOK. The length $L_{LC\_d}$ of the linear component LC may be in the range of, for example, several millimeters (e.g., 3-7 millimeters, or more particularly, 4-5 millimeters). The material that forms the connector 230d may have a thickness $T_{LC\_d}$ of, for example, one or more millimeters (e.g., 1-7 millimeters, or more particularly, 2-3 millimeters), the hook HOOK may have a diameter $D_{H\_d}$ of, for example, one or more millimeters (e.g., 1-7 millimeters, or more particularly, 2-3 millimeters), and the cup CUP may have a diameter $D_{C\_d}$ of one or more millimeters (e.g., 1-7 millimeters, or more particularly, 2-3 millimeters). The thickness $T_{LC\_d}$, and/or the length of the linear component LC of the connector 230d may be determined based on a distance between the anchor stud 210 and the support stud 220 to which it is connected, as well as an amount of pressure that is to be applied to the anchor stud 210 and the support stud 220, and an elasticity of the material forming the connector 230b.

The disclosed embodiments are not limited to those illustrated in FIGS. 7A-7D. Connector 230 may include ends with any combination of a loop LOOP, a cup CUP, or a HOOK. Similarly, the linear component LC may be a single long loop (e.g., linear component LC of FIG. 7A), multiple connected loops (e.g., linear component LC of FIG. 7B), a single linear piece (e.g., linear components LC of FIGS. 7C and 7D), or any combination thereof.

Figure 8:
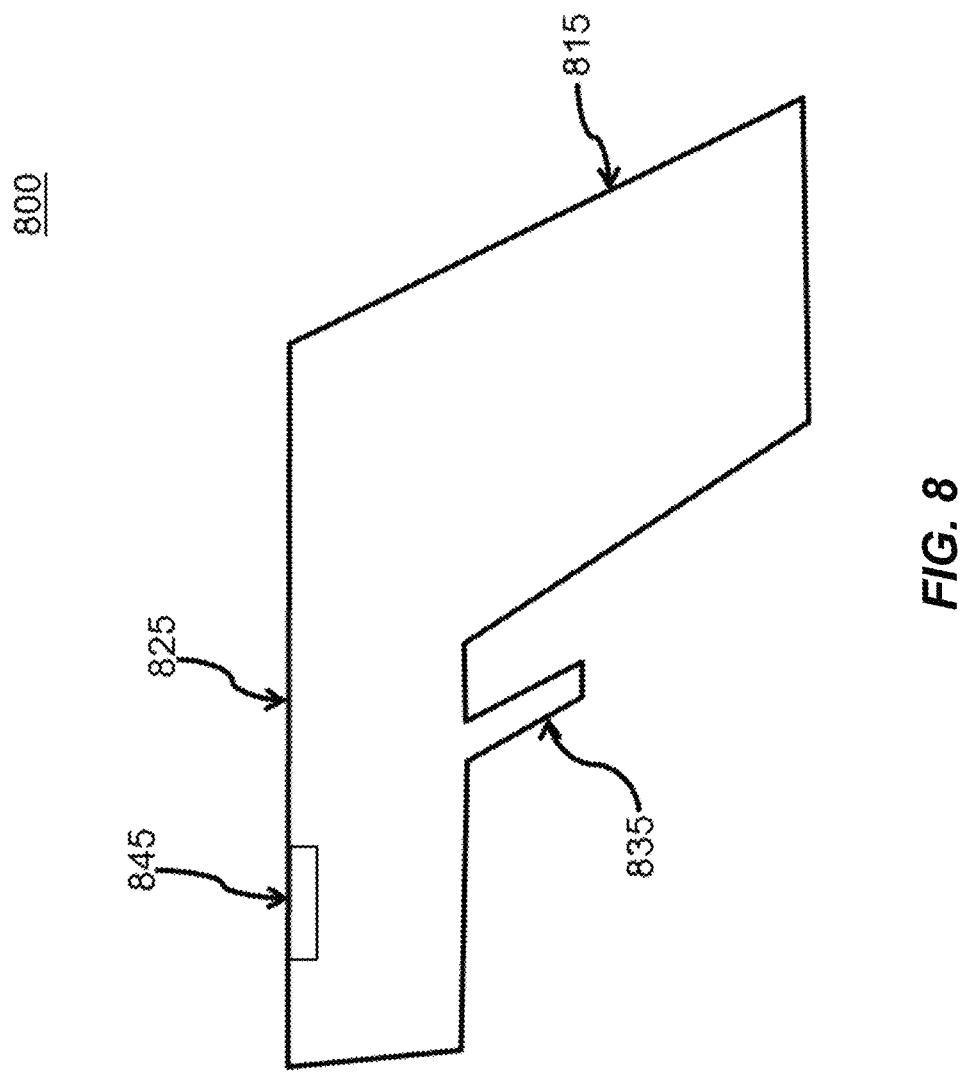
FIG. 8 is a block diagram of an oral stud placement gun, according to certain exemplary embodiments.

FIG. 8 illustrates an oral stud placement gun 800, according to certain exemplary embodiments. As shown in FIG. 8, an oral stud placement gun 800 may include a handle 815, a barrel 825, a trigger 835, and a load receptacle 835. Although not illustrated in FIG. 8, the oral stud placement gun 800 may also include a blade, blade movement mechanisms, and a suction mechanism. In some embodiments, an oral stud 400 may be loaded in the barrel 825 of the oral stud placement gun 800 through a load receptacle 845. The load receptacle 845 may be an opening in the top of the barrel 825 of a sufficient shape and size sufficient to place an oral stud 400 into the barrel 825. In other embodiments, an oral stud 400 may be loaded in the gun 800 via the front end of the barrel 825. In such an embodiment, the oral stud 400 may be placed in the front end of the barrel 825 of the gun 800 and pressed in the direction of the handle 815.

As discussed further below, the oral stud placement gun 800 may provide for suction using the suction mechanism, to draw a patient's tissue against the end of the barrel 825, and hold the patient's tissue firmly against the end of the barrel 825. When the handle 815 is held in the palm of the user's hand and the user applies pressure to the trigger 835, the blade movement mechanism may begin execution, causing the blade to move through the barrel 825 in a direction from the handle 815 toward the end of the barrel 825. As the blade advances through the barrel 825, it may pass through the center of the oral stud 400 loaded in the barrel 825, and push the oral stud 400 forward out of the end of the barrel 825 into the anchor site or support site.

Figure 9A:
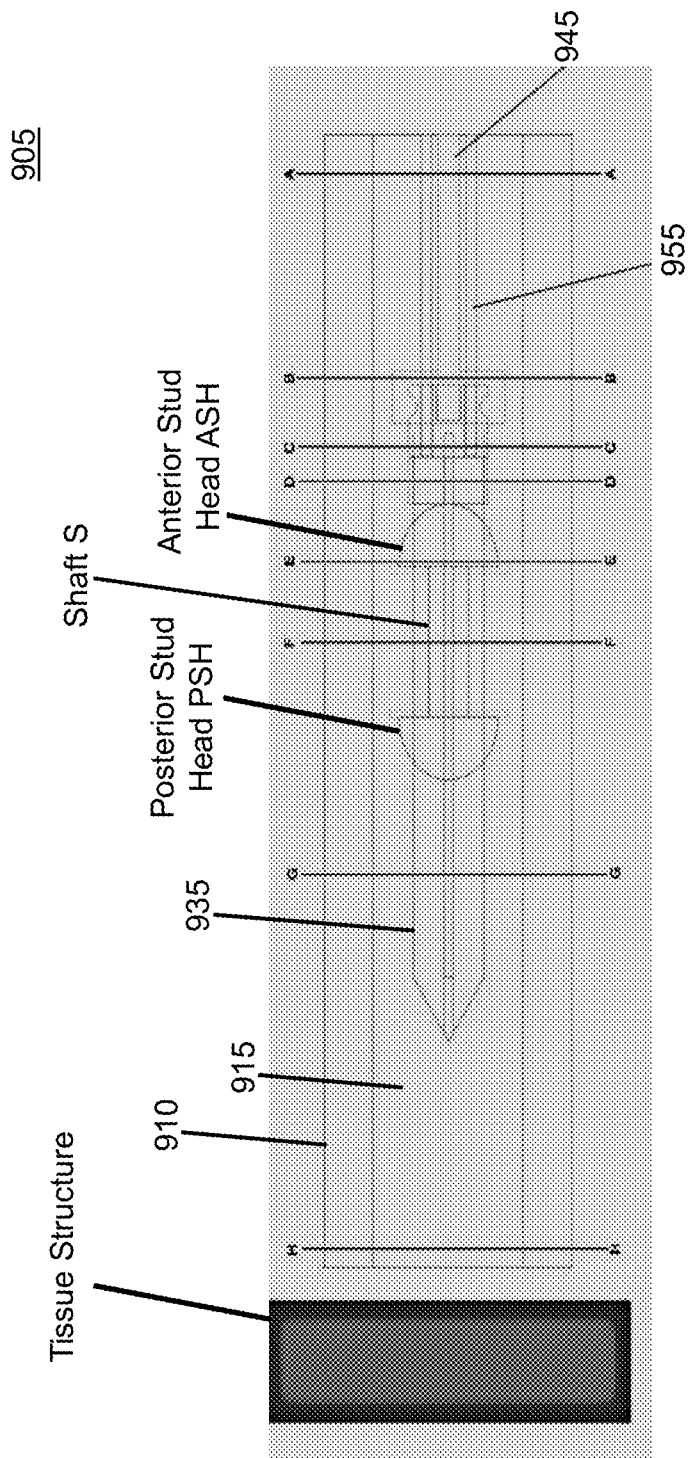
FIG. 9A is a schematic illustrating the barrel of an oral stud placement gun loaded with an oral stud, according to certain exemplary embodiments.

FIG. 9A is a schematic illustrating the arrangement of a blade and oral stud loaded in a barrel of an oral stud placement gun, such as the oral stud placement gun 800 of FIG. 8, according to certain exemplary embodiments. FIGS. 9B-9I are schematics illustrating a blown up views of cross-sections A-A, B-B, C-C, D-D, E-E, F-F, G-G, and H-H, respectively, of FIG. 9A, according to some exemplary embodiments.

Referring to FIG. 9A, an oral stud placement gun may include a barrel 905 having a hollow cylinder 915 surrounded by a housing 910. In the embodiment of FIG. 9A, the barrel 905 may be round, and the hollow cylinder 915 and housing 910 may be concentrically placed along a central axis of the barrel 905. At a rear portion, the barrel 905 may further include a blade drive shaft 945 and a plurality of stud drive shafts 955. When the barrel 905 is loaded with an oral stud 925, the blade drive shaft 945 and plurality of stud drive shafts 955 may be adjacent to the anterior stud head ASH, which may be the accessible portion of the stud for the connector 230 that is not projected through the patient's tissue. The oral stud 925 may be an anchor stud 210 or a support stud 220.

Figure 9C:
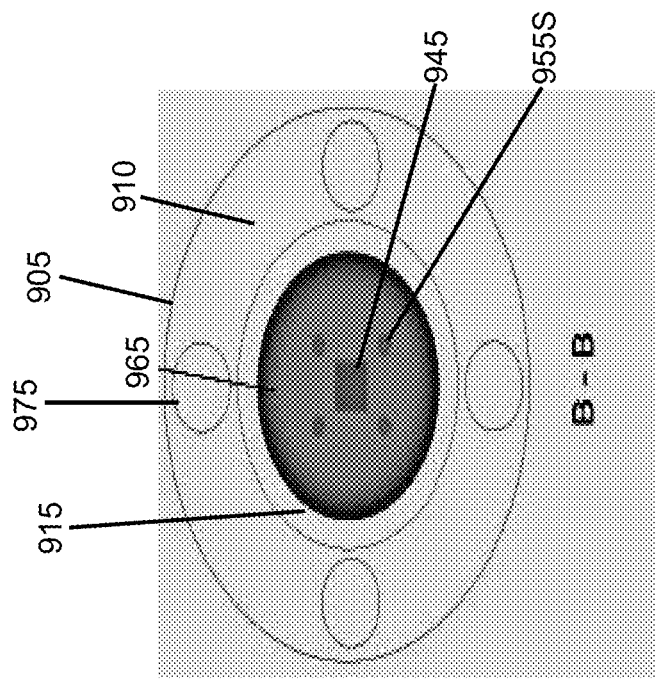
FIG. 9C is a schematic illustrating a blown up view of cross-section B-B of FIG. 9A and a stud drive shaft and a blade drive shaft, according to some exemplary embodiments.
Figure 9B:
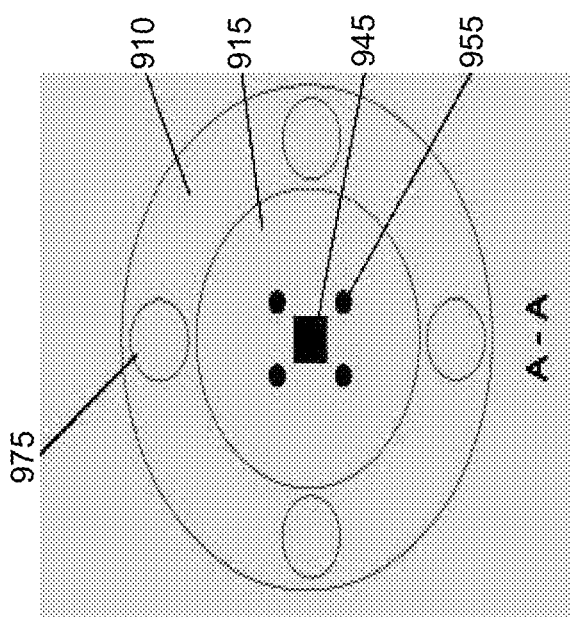
FIG. 9B is a schematic illustrating a blown up view of cross-section A-A of FIG. 9A and a stud drive shaft and a blade drive shaft, according to some exemplary embodiments.

As shown in FIG. 9B, which is a cross-section along line A-A of FIG. 9A, the housing 910 may include a plurality of suction holes 975 (e.g., four). The suction holes 975 may be used to provide a suction force when the barrel 905 is pressed against a target (anchor) site or a support site. In the embodiment of FIG. 9B, the blade drive shaft 945 may be located along a central axis of the barrel 905, and may be surrounded be the plurality of stud drive shafts 955. The stud drive shafts 955 may be placed at equal distances from the blade drive shaft 945 and each other.

Figure 9E:
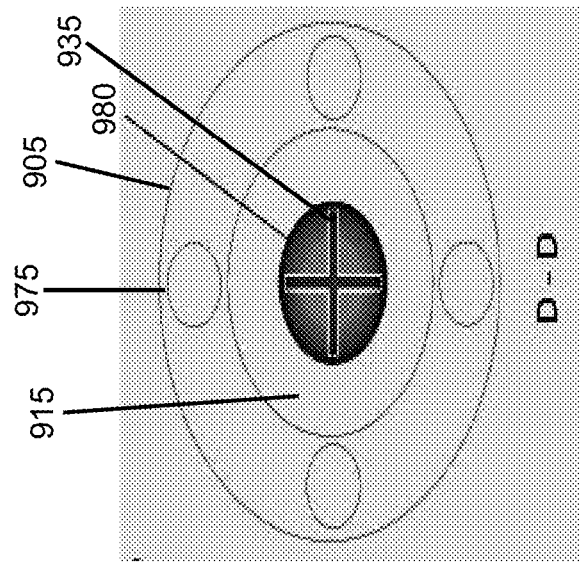
FIG. 9E is a schematic illustrating a blown up view of cross-section D-D of FIG. 9A and a stud drive shaft and a blade drive shaft, according to some exemplary embodiments.
Figure 9D:
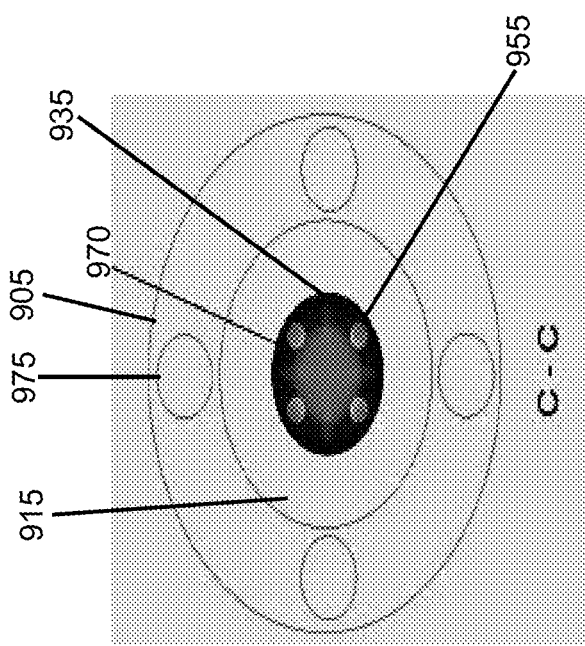
FIG. 9D is a schematic illustrating a blown up view of cross-section C-C of FIG. 9A and a stud drive shaft and a blade drive shaft, according to some exemplary embodiments.

As shown in FIGS. 9C and 9D, which are cross-section along lines B-B and C-C, respectively, of FIG. 9A, a blade hub holding member 965 may be provided to hold a blade hub 970. The blade hub holding member 965 and the blade drive shaft 945 may be mechanically mated to one another such that the blade hub holding member 965 and the blade drive shaft 945 move as one unit. The blade hub holding member 965 may be formed to substantially fill the hollow cylinder 915 of the barrel 905. For example, the blade hub holding member 965 may have a diameter than is slightly smaller than the interior diameter of the hollow cylinder 915, such that the edges of blade hub holding member 965 nearly touch the hollow cylinder 915 along the circumference of the blade hub holding member 965, thereby allowing the blade hub holding member 965 to move unimpeded through the hollow cylinder 915. As shown in FIG. 9D, the blade hub 970 may include several cavities 955S that allow each of the corresponding stud drive shafts 955 to move separately from the blade drive shaft 945. The cavities 955S may be empty spaces (e.g., hollow tubes) through which the stud drive shafts 955 advance forward and backward. The blade hub 970 may hold the blade 935, and may control the extension and retraction of the blade 935. The blade hub holding member 965 and blade hub 970 may be formed of plastic.

As shown in FIG. 9E, which is a cross-section along line D-D of FIG. 9A, a sliding stud displacement member 980. The sliding stud displacement member 980 may be configured to move forward and backward along the central axis of the barrel 905. For example, the sliding stud displacement member 980 may provide pressure against an oral stud 925 loaded in the barrel 905, pushing the oral stud 925 toward and through the target (anchor) or support site. The sliding stud displacement member 980 may have an opening that allows for the blade 935 to move through the sliding stud displacement member 980 and to the oral stud 925.

Figure 9G:
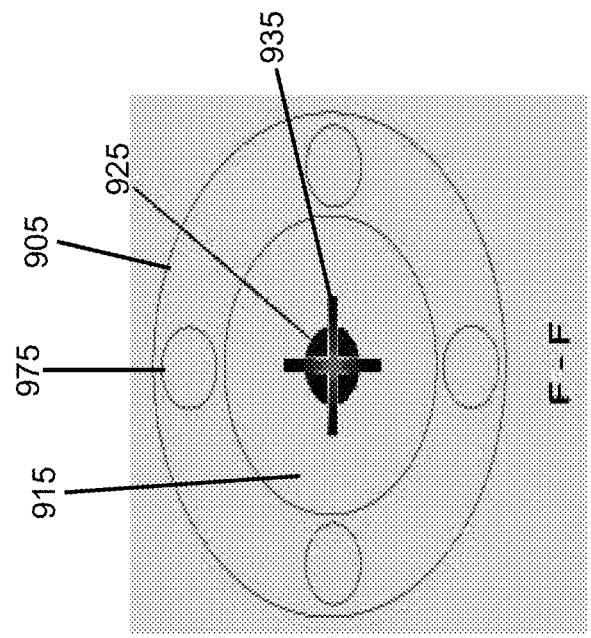
FIG. 9G is a schematic illustrating a blown up view of cross-section F-F of FIG. 9A and a stud drive shaft and a blade drive shaft, according to some exemplary embodiments.
Figure 9F:
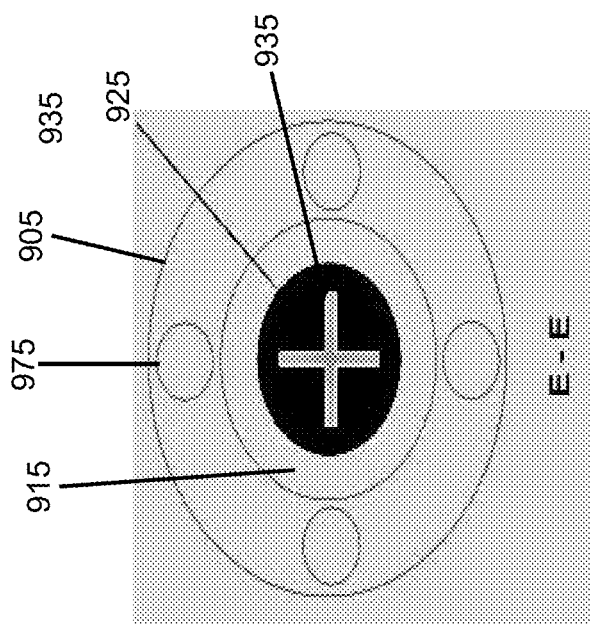
FIG. 9F is a schematic illustrating a blown up view of cross-section E-E of FIG. 9A and a stud drive shaft and a blade drive shaft, according to some exemplary embodiments.

FIGS. 9F and 9G, which are cross-sections along lines E-E and F-F, respectively, of FIG. 9A, illustrate placement of the blade 935 along a central axis of the oral stud 925. Specifically, FIG. 9F is a cross-section of the blade 935 passing through the anterior stud head ASH of the oral stud 925, and FIG. 9G is a cross-section of the blade 935 passing through the shaft S of the oral stud 925. In the embodiments illustrated by FIGS. 9A-9I, the height $H_B$ and width $W_B$ of the blade 935 may be smaller than a diameter $D_{CP}$ of a circular plate CP of the anterior stud head ASH, and larger than, the same as, or smaller than a diameter $D_S$ of the shaft S of the oral stud 925.

Figure 9I:
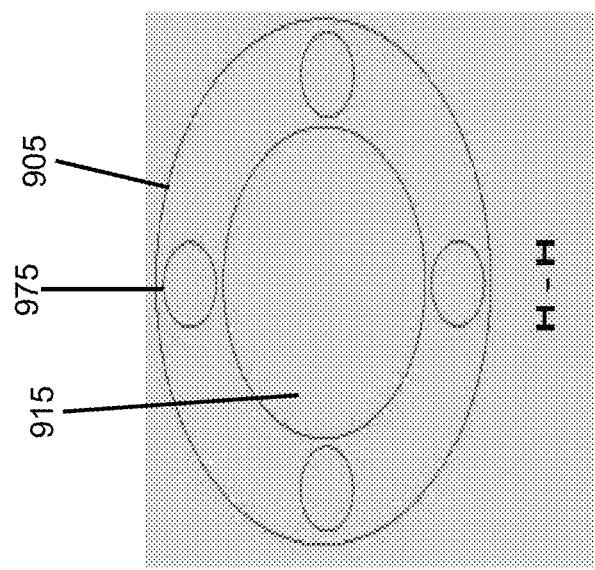
FIG. 9I is a schematic illustrating a blown up view of cross-section H-H of FIG. 9A and a stud drive shaft and a blade drive shaft, according to some exemplary embodiments.
Figure 9H:
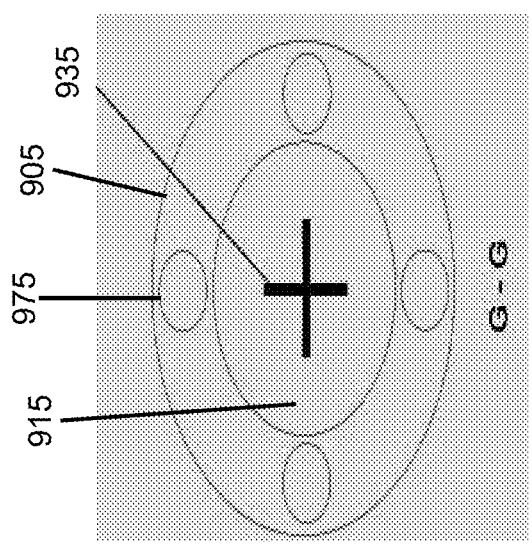
FIG. 9H is a schematic illustrating a blown up view of cross-section G-G of FIG. 9A and a stud drive shaft and a blade drive shaft, according to some exemplary embodiments.

FIG. 9H, which is a cross-section along line G-G of FIG. 9A, illustrates the advancement of the blade 935 through the barrel 905. As shown in FIG. 9H, the blade 935 advances through the barrel 905 ahead of the oral stud 925 to allow for the blade to pierce the target (anchor) or support site, making a hole in the target (anchor) or support site, before the oral stud 925 is advanced through the target (anchor) or support site.

FIG. 9I, which is a cross-section of line H-H of FIG. 9A, illustrates a face-on view of the barrel 905. As shown in FIG. 9I, the suction holes 975 extend through the length of the barrel 905 and are concentrically open to the target (anchor) or support site. For example, when the barrel 905 is centered over and contacts the target (anchor) or support site, a suction force is applied concentrically to the area surrounding target (anchor) or support site, drawing the area around the target (anchor) or support site firmly against the barrel 905. The suction force exerted by the suction holes 975 may create an air-tight seal of the suction holes 975 with the tissue surrounding the target (anchor) or support site, thereby preventing relative movement of the target (anchor) or support site with respect to the barrel 905.

Figure 10:
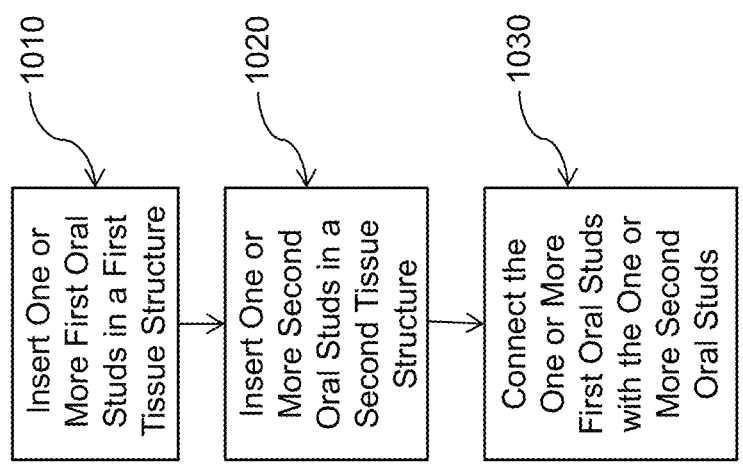
FIG. 10 is a flowchart of a method of suspension uvulopalatopexy using a multi-component device, according to certain exemplary embodiments.

FIG. 10 is a flowchart of a method of suspension uvulopalatopexy using a multi-component device, according to certain exemplary embodiments. FIGS. 11-14 are schematics illustrating the steps of FIG. 10. The systems and methods for suspension uvulopalatopexy, as disclosed and described herein, may include two or more oral studs 925 and one or more elastic connectors 230 (e.g., as illustrated in FIGS. 2A-2G). The oral studs 925 and elastic connectors 230 may work together to affect a position of the soft palate 102, the tongue 112, and/or the lateral pharyngeal walls 117. For example, in some cases, the oral studs 925 and elastic connectors 230 may bring the uvula 104, the tongue 112, and/or lateral pharyngeal walls 117 forward, thereby preventing the air passageway between soft palate 102 and oropharynx 115 from becoming narrow or blocked.

Referring to FIG. 10, one or more first oral studs 925 (e.g., support studs 220) may be inserted into a first tissue structure (e.g., the uvula 103, the tongue 112, and/or the lateral pharyngeal walls 117) (step 1010). The one or more support studs 220 may be inserted using a mechanized device, such as the exemplary oral stud placement gun 800 discussed above.

Figure 11:
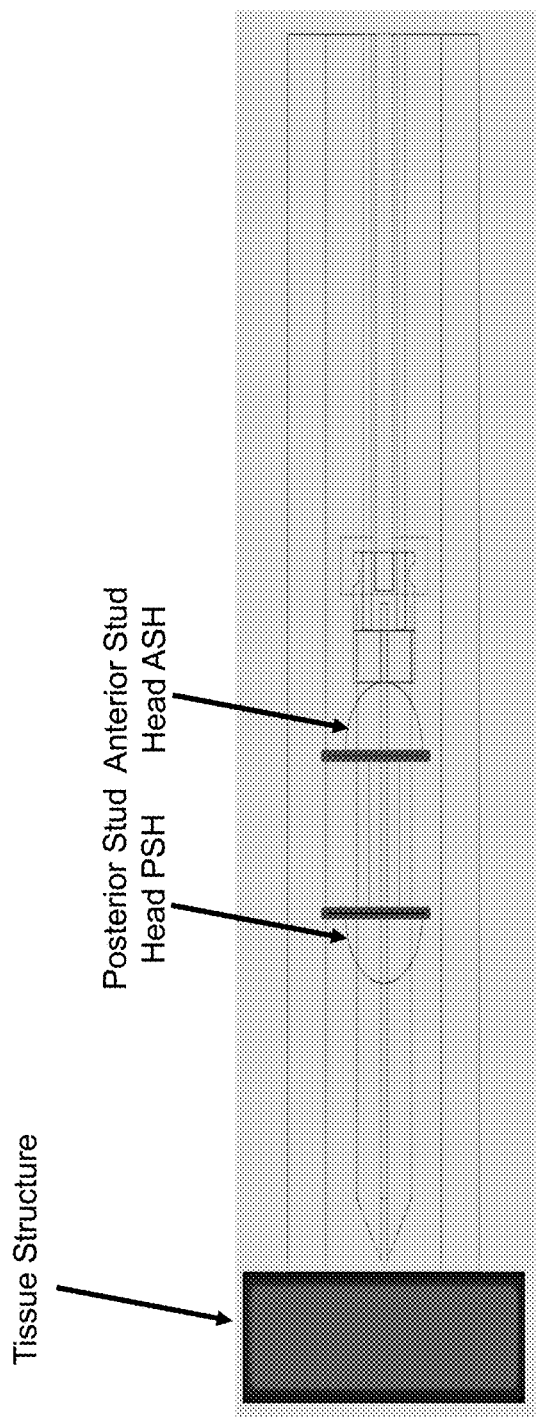
FIG. 11 illustrates an oral stud loaded in an oral stud placement gun when it is placed in contact with an anchor or support site, according to certain exemplary embodiments.
Figure 12:
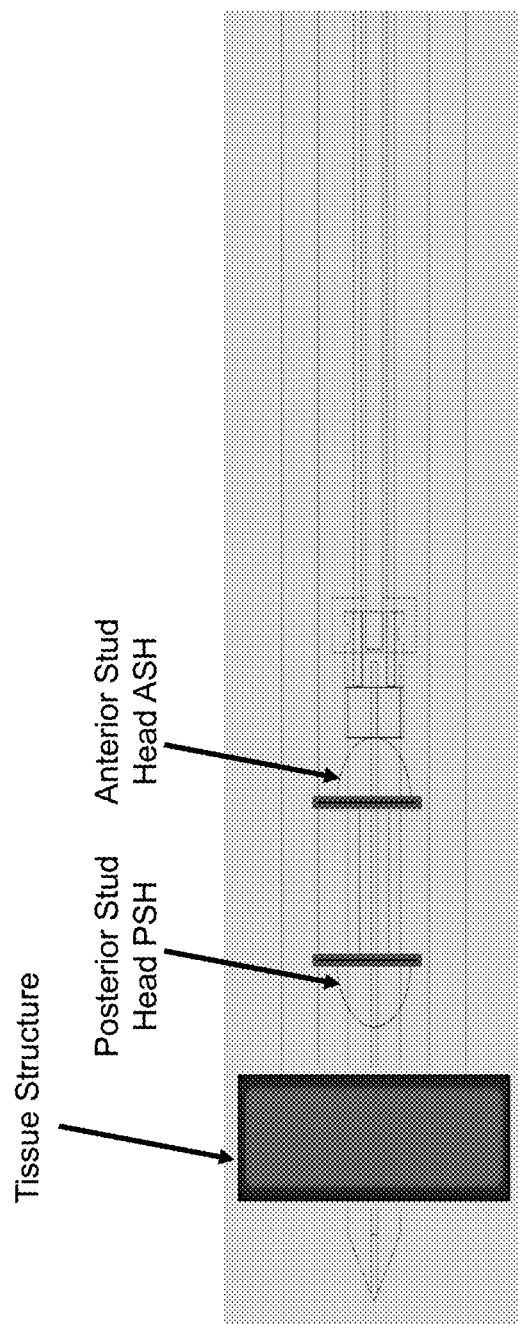
FIG. 12 illustrates an oral stud loaded in an oral stud placement gun when it is engaged with an anchor or support site, according to certain exemplary embodiments.
Figure 13:
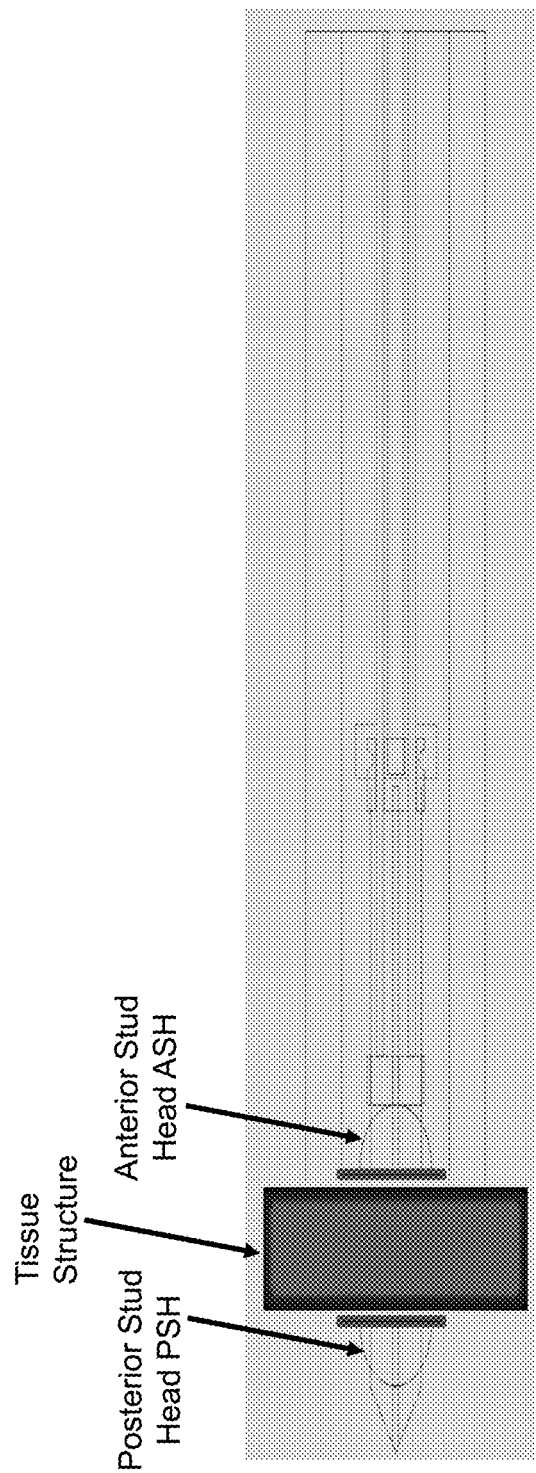
FIG. 13 illustrates an oral stud loaded in an oral stud placement gun when it advances through an anchor or support site, according to certain exemplary embodiments.
Figure 14:
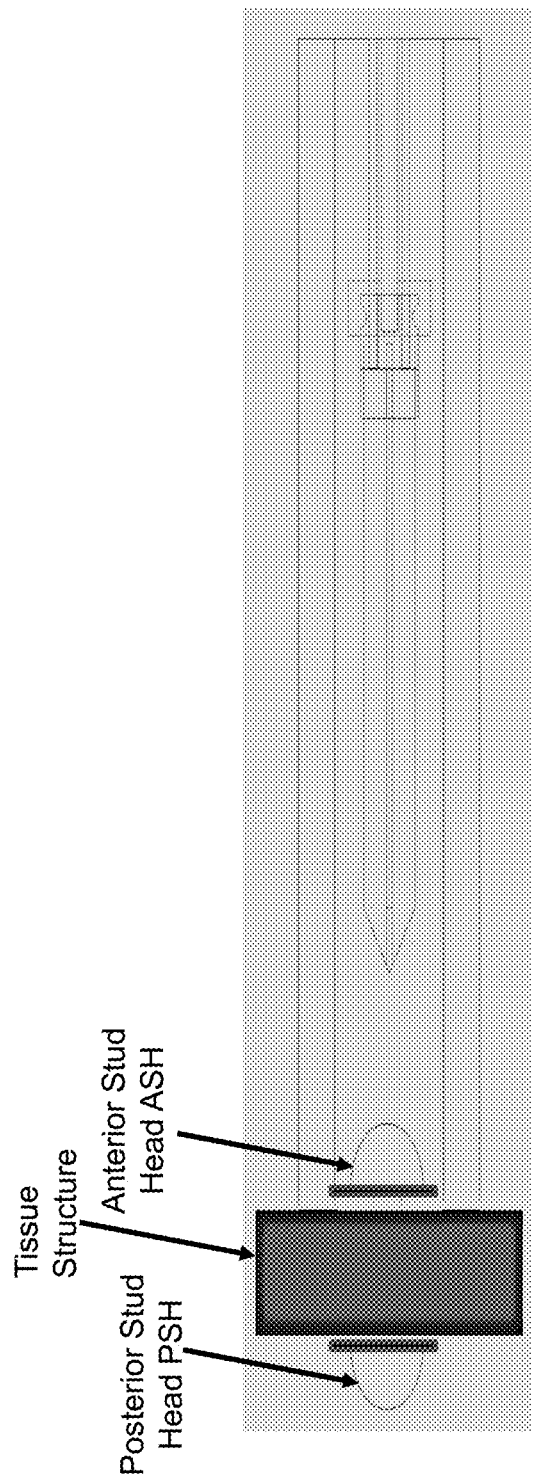
FIG. 14 illustrates an oral stud loaded in an oral stud placement gun when it is deployed into an anchor or support site, according to certain exemplary embodiments.

As shown in FIG. 11, when the barrel 905 of the oral stud placement gun 800 is placed in contact with the target (anchor) or support site, the suction holes 975 located in the housing 910 may engage with tissue of the tissue structure, holding the tissue structure firmly against the barrel 905. Then, as shown in FIG. 12, the blade drive shaft 945 may engage, causing the blade 935 to extend through the front portion of the barrel 905, and incise the tissue structure, thereby forming an opening in the tissue structure. Next, as shown in FIG. 13, the stud drive shafts 955 and sliding stud displacement member 980 may engage, causing the oral stud 925 to move through the barrel 905, and advance through the opening in the tissue structure formed by the blade 935. Finally, as shown in FIG. 14, when the oral stud 935 is deployed in the tissue structure, the blade 935 may retract within the barrel 905, allowing for another oral stud 925 to be loaded into the oral stud placement gun 800.

Returning to FIG. 10, one or more second oral studs 925 (e.g., anchor studs 210) may be inserted into a second tissue structure (e.g., the soft palate 102) (step 1020). Similarly to step 1010, the one or more oral studs 925 may be inserted using a mechanized device, such as the oral stud placement gun 800. In some embodiments, as reflected in FIGS. 11-14, the mechanized device may be configured to hold the tissue structure, incise the tissue structure, and advance an oral stud 925 into a predetermined location of the tissue structure.

Finally, the one or more first oral studs 925 may be connected to one or more second oral studs 925 via one or more connectors 230 (step 1030). The one or more first and second oral studs 925 are connected with one or more elastic connectors 230 external to the tissue of the tissue structure. In some embodiments, the one or more connectors 230 may be attached to and/or detached from the one or more oral studs 925 by hand (e.g., using one or more fingers to hold and attach/detach the connectors 230) or using a mechanical tool (e.g., an insertion/extraction hook or device). The one or more of the connectors 230 may be replaced in a similar manner. The attachment of the one or more connectors 230 to the one or more oral studs 925 may pull the soft palate 102, the tongue 112, and/or the lateral pharyngeal walls 117 away from the airway to help with snoring and/or sleep apnea. Examples of the connections formed between the one or more first and second oral studs 925 are discussed above in connection with FIGS. 2A-2I and FIGS. 3A-3B. Example connectors 230 are discussed further above in connection with FIGS. 7A-7D.

Figure 15B:
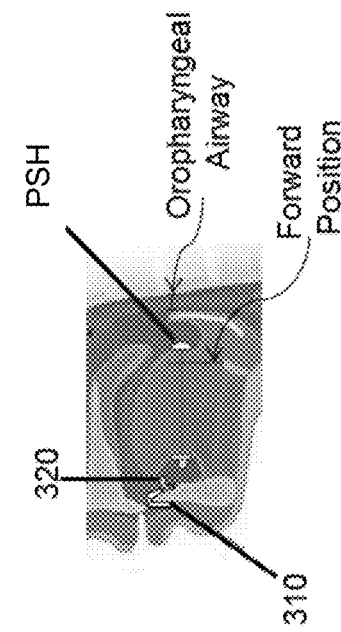
FIGS. 15A-15C are side views illustrating suspension glossomandibulopexy using a multi-component device, according to certain exemplary embodiments.
Figure 15A:
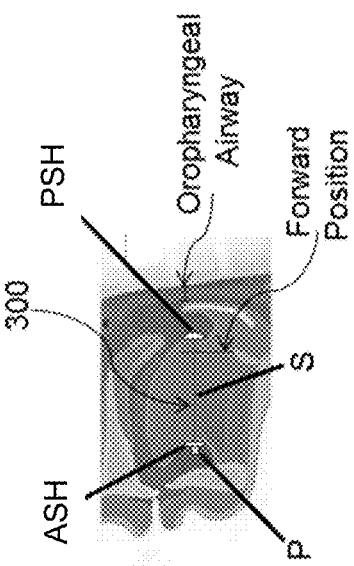
Figure 15C:
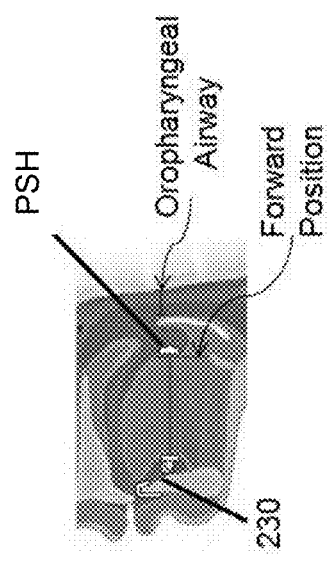

FIGS. 15A-15C are cross-sectional of a human head to illustrate placement of components of a multi-component device used in suspension glossomandibulopexy, consistent with certain exemplary embodiments. Specifically, FIGS. 15A-15C illustrate an embodiment in which an oral stud 300 is inserted into the tongue 112, bringing the tongue 112 forward in the oral cavity 111 and increasing the space in the oropharynx 115. In the embodiment illustrated by FIGS. 15A-15C, the multi-component device includes one oral stud 300 inserted into a tongue 112, a dental anchor 310 attached to or inserted into a structure that provides support, and one or more external elastic connectors 230 that mechanically couple the oral studs 300 to the dental anchor 310. As illustrated in FIGS. 15A-15C, the oral stud 300, dental anchor 310, and elastic connector 230 may maintain a position of, or bring forward, the tongue 112 in the oral cavity 111, thereby maintaining an open passage through the oropharynx 115. In the embodiments of FIGS. 15A-15C, the oral stud 300 includes a shaft S (or suture), a posterior stud head PSH, an anterior stud head ASH, and a projection P attached to the anterior stud head ASH.

As shown in FIG. 15A, the oral stud 300 may inserted into the tongue 112 at a midline of the tongue 112. The oral stud 300 may be inserted such that the posterior stud head PSH is projected through the posterior aspect of the tongue 112, passing through the tissue of the tongue 112, to protrude from the posterior aspect of the tongue 112 near the epiglottis 105. When the oral stud 300 is fully inserted into the tongue, the posterior stud head PSH and the anterior stud head ASH may be external to the tissue of the tongue 112, and the shaft S (or suture) may be internal to the tissue of the tongue 112. Referring to FIG. 15B, a dental anchor 310 may be placed in the oral cavity 111. In the embodiment of FIGS. 15A-15C, the dental anchor 310 may be removably attached to a patient's teeth (e.g., placed over the patient's teeth), such that the patient's teeth hold the dental anchor 310 firmly in place. In this manner, the dental anchor 310 may be inserted and/or removed from the patient's oral cavity 111, as desired. The dental anchor 310 and the oral stud 300 may be connected to one another with a connector 230 external to the tongue 112.

The disclosed embodiments may minimize the amount of implanted material thus decreasing the risk for interference with the functional integrity of the structure, as well as, minimizing the chance for foreign body complications such as scarring and "foreign body" inflammatory reactions/extrusion.

The present disclosure is not to be limited in terms of the particular embodiments described in this application, which are intended as illustrations of various aspects. Many modifications and variations can be made without departing from its spirit and scope, as will be apparent. Functionally equivalent methods and apparatuses within the scope of the disclosure, in addition to those enumerated herein, will be apparent from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The foregoing description, along with its associated embodiments, has been presented for purposes of illustration only. It is not exhaustive and does not limit the invention to the precise form disclosed. Those skilled in the art will appreciate from the foregoing description that modifications and variations are possible in light of the above teachings or may be acquired from practicing the disclosed embodiments. For example, the steps described need not be performed in the same sequence discussed or with the same degree of separation. Likewise various steps may be omitted, repeated, or combined, as necessary, to achieve the same or similar objectives. Accordingly, the invention is not limited to the above-described embodiments, but instead is defined by the appended claims in light of their full scope of equivalents.

What is claimed is:

1. A method for treatment of snoring and obstructive sleep apnea, comprising:
   inserting a first retractor member in a form of a stud into a predetermined location in a region of a uvula, wherein the first retractor member includes a stud shaft, an anterior stud head, and a posterior stud head, wherein the anterior and posterior stud heads of the first retractor member are respectively located on external surfaces in the region of the uvula at opposite ends of the stud shaft of the first retractor member, and wherein the stud shaft of the first retractor member is positioned within soft tissue of the uvula;
   inserting an anchor member in a form of a stud into a predetermined location in a region of a superior soft palate, wherein the anchor member includes a stud shaft, an anterior stud head, and a posterior stud head, wherein the anterior and posterior stud heads of the anchor member are respectively located on external surfaces in the region of the superior soft palate at opposite ends of the stud shaft of the anchor member, and wherein the stud shaft of the anchor member is positioned within soft tissue in the region of the superior soft palate;
   connecting, via an external elastic band, the first retractor member with the anchor member, wherein the external elastic band has a first connecting piece detachably connected to the anterior stud head of the first retractor member and a second connecting piece detachably connected to the anterior stud head of the anchor member;
   inserting a second retractor member in the region of the uvula, and
   connecting, via a second external elastic band, the second retractor member with the anchor member,
   wherein the second external elastic band has a first connecting piece detachably connected to an anterior stud head of the second retractor and a second connecting piece detachably connected to the anterior stud head of the anchor member,
   wherein the first retractor member is located lateral to a midline in the region of the uvula and the second retractor member is located contralateral to the midline in the region of the uvula, and
   wherein the first retractor member and the anchor member are discrete members that are reversibly connected via the external elastic band.

2. The method of claim 1,
   wherein the predetermined location of the first retractor member is at a midline in the region of the uvula, and
   wherein the predetermined location of the anchor member is at a midline in the region of the superior soft palate.

3. The method of claim 1,
   wherein the anterior stud head of the first retractor member is located in an oral cavity of a patient, and
   wherein the posterior stud head of the retractor member is located in an oropharynx of the patient.

4. The method of claim 1,
   wherein the anterior stud head of the anchor member is located in an oral cavity of a patient, and
   wherein the posterior stud head of the anchor member is located in a nasopharynx of the patient.

5. The method of claim 1, wherein the first retractor member and the anchor member are each formed of a bio-compatible material.

6. The method of claim 1, wherein the external elastic band is formed of a bio-compatible elastic material.

7. A method for treatment of snoring and obstructive sleep apnea, comprising:
   inserting a first oral retractor member into a first location of an oral structure targeted for retraction, wherein the first oral retractor member includes a stud shaft, an anterior stud head, and a posterior stud head, wherein the anterior and posterior stud heads of the first oral retractor member are respectively located on external surfaces of the oral structure targeted for retraction at opposite ends of the stud shaft, and wherein the stud shaft is positioned within soft tissue of the oral structure targeted for retraction;
   inserting a first oral anchor member into a first location of an oral anchor structure, wherein the first oral anchor member includes a stud shaft, an anterior stud head, and a posterior stud head, wherein the anterior and posterior stud heads are respectively located on external surfaces of the oral anchor structure at opposite ends of the stud shaft, and wherein the stud shaft is positioned within soft tissue of the oral anchor structure; and
   connecting, using at least one first detachable external elastic band, the anterior stud head of the first oral retractor member with the anterior stud head of the first oral anchor member;
   inserting a second oral retractor member into a second location of the oral structure targeted for retraction, wherein the second oral retractor member includes a stud shaft, an anterior stud head, and a posterior stud head, wherein the anterior and posterior stud heads of the second oral retractor member are respectively located on external surfaces of the oral structure targeted for retraction at opposite ends of the stud shaft, and wherein the stud shaft is positioned within the soft tissue of the oral structure targeted for retraction;
   inserting a second oral anchor member into a second location of the oral anchor structure, wherein the second oral anchor member includes a stud shaft, an anterior stud head, and a posterior stud head, wherein the anterior and posterior stud heads of the second oral anchor member are respectively located on external surfaces of the oral anchor structure at opposite ends of the stud shaft, and wherein the stud shaft is positioned within the soft tissue of the anchor structure; and connecting, using at least a second detachable external elastic band, the anterior stud head of the second oral retractor member with the anterior stud head of the second oral anchor member.

8. The method of claim 7,
wherein the oral structure targeted for retraction is in a region of a uvula and the oral anchor structure is in a region of a superior soft palate,
wherein the first location of the oral structure targeted for retraction is at a midline in the region of the uvula, and
wherein the first location of the oral anchor structure is at a midline in the region of the superior soft palate.

9. The method of claim 7,
wherein the first location of the oral structure targeted for retraction is in a region of a uvula, and
wherein the first location of the oral anchor structure is in a region of a superior soft palate.

10. The method of claim 7,
wherein the oral anchor structure is a tongue and the oral structure targeted for retraction is in a region of a uvula,
wherein the first location of the oral anchor structure is at a midline of the tongue, and
wherein the first location of the oral structure targeted for retraction is at a midline in the region of the uvula.

11. The method of claim 7, further comprising:
inserting a second oral anchor member into a second location of the oral anchor structure, wherein the second oral anchor member includes a stud shaft, an anterior stud head, and a posterior stud head, wherein the anterior and posterior stud heads of the second oral anchor member are respectively located on external surfaces of the oral anchor structure at opposite ends of the stud shaft, and wherein the stud shaft is positioned within the soft tissue of the oral anchor structure; and
connecting, using at least a second detachable external elastic band, the anterior stud head of the first oral retractor member with the anterior stud head of the second oral anchor member.

12. The method of claim 11,
wherein the oral structure targeted for retraction is in a region of a uvula and the oral anchor structure is in a region of a superior soft palate,
wherein the first location of the oral structure targeted for retraction is at a midline of the uvula,
wherein the first location of the oral anchor structure is offset from a midline of the superior soft palate, and
wherein the second location of the oral anchor structure is offset from the midline of the superior soft palate contralateral to the first location of the oral anchor structure.

13. The method of claim 11,
wherein the oral anchor structure is a tongue and the oral structure targeted for retraction is in a region of a uvula,
wherein the first location of the oral anchor structure is at a midline of the tongue,
wherein the first location of the oral structure targeted for retraction is offset from a midline in the region of the uvula, and
wherein the second location of the oral structure targeted for retraction is offset from the midline in the region of the uvula contralateral to the first location of the oral structure targeted for retraction.

14. The method of claim 7, further comprising:
inserting a second oral retractor member into a second location of the oral structure targeted for retraction, wherein the second oral retractor member includes a stud shaft, an anterior stud head, and a posterior stud head, wherein the anterior and posterior stud heads are respectively located on external surfaces of the oral structure targeted for retraction at opposite ends of the stud shaft, and wherein the stud shaft is positioned within the soft tissue of the oral structure targeted for retraction; and
connecting, using at least one second detachable external elastic band, the anterior stud head of the second oral retractor member with the anterior stud head of the first oral anchor member.

15. The method of claim 14,
wherein the first location of the oral anchor structure is a lateral pharyngeal wall,
wherein the second location of the oral anchor structure is a contralateral lateral pharyngeal wall, and
wherein the oral structure targeted for retraction is in a region of a uvula, and the first location of the oral structure targeted for retraction is at a midline in the region of the uvula.

16. The method of claim 14,
wherein the oral anchor structure is a tongue and the oral structure targeted for retraction is in a region of a uvula,
wherein the first location of the oral anchor structure is offset from a midline of the tongue,
wherein the second location of the oral anchor structure is offset from the midline of the tongue contralateral to the first location of the oral anchor structure,
wherein the first location of the oral structure targeted for retraction is at a midline of a palate.

17. The method of claim 7,
wherein the oral anchor structure comprises lateral pharyngeal walls and the oral structure targeted for retraction is in a region of a uvula,
wherein the first location of the oral anchor structure is a lateral pharyngeal wall,
wherein the second location of the oral anchor structure is a contralateral lateral pharyngeal wall,
wherein the first location of the oral structure targeted for retraction is offset from a midline in the region of the uvula, and
wherein the second location of the oral structure targeted for retraction is offset from the midline of the oral structure targeted for retraction contralateral to the first location of the oral structure targeted for retraction.

18. The method of claim 7,
wherein the oral anchor structure comprises a tongue and the oral structure targeted for retraction is in a region of a uvula,
wherein the first location of the oral anchor structure is offset from a midline of the tongue,
wherein the second location of the oral anchor structure is offset from the midline of the tongue contralateral to the first location of the oral anchor structure,
wherein the first location of the oral structure targeted for retraction is offset from a midline in the region of the uvula, and
wherein the second location of the oral structure targeted for retraction is offset from the midline in the region of the uvula contralateral to the first location of the oral structure targeted for retraction.

19. The method of claim 7, wherein the first oral retractor member and the first oral anchor member are each formed of a bio-compatible elastic material.

20. The method of claim 1,
wherein the first retractor member includes a circular plate and a projection formed on one side of the circular plate, the projection having one of a rounded notched shape, a hook shape, or a loop shape, wherein the anchor member includes a circular plate and a projection formed on one side of the circular plate, the projection having one of a rounded notched shape, a hook shape, or a loop shape, and wherein connecting the first retractor member with the anchor member comprises:

connecting the first connecting piece of the external elastic band to the projection of the first retractor member; and connecting the second connecting piece of the external elastic band to the projection of the anchor member to connect the first retractor member with the anchor member.

21. The method of claim 1, wherein the stud shaft of the first retractor member and the stud shaft of the anchor member are comprised of an elastic material.

\* \* \* \* \*